US012637644B2

(12) United States Patent
Nielson

(10) Patent No.: US 12,637,644 B2
(45) Date of Patent: *May 26, 2026

(54) THREE-DIMENSIONAL SILICON SCAFFOLD FOR TISSUE ENGINEERING

(71) Applicant: Nielson Scientific, LLC, Lehi, UT (US)

(72) Inventor: Gregory Nolan Nielson, Lehi, UT (US)

(73) Assignee: Nielson Scientific, LLC, Lehi, UT (US)

( * ) Notice: Subject to any disclaimer, the term of this patent is extended or adjusted under 35 U.S.C. 154(b) by 1437 days.

This patent is subject to a terminal disclaimer.

(21) Appl. No.: 16/642,397

(22) PCT Filed: Sep. 5, 2018

(86) PCT No.: PCT/US2018/049543
§ 371 (c)(1),
(2) Date: Feb. 27, 2020

(87) PCT Pub. No.: WO2019/050947
PCT Pub. Date: Mar. 14, 2019

(65) Prior Publication Data
US 2020/0190452 A1 Jun. 18, 2020

Related U.S. Application Data

(60) Provisional application No. 62/618,205, filed on Jan. 17, 2018, provisional application No. 62/554,488, filed on Sep. 5, 2017.

(51) Int. Cl.
*C12M 3/00* (2006.01)
*B23K 26/00* (2014.01)
(Continued)

(52) U.S. Cl.
CPC ......... *C12M 21/08* (2013.01); *B23K 26/0006* (2013.01); *B23K 26/362* (2013.01);
(Continued)

(58) Field of Classification Search
CPC ............. C25F 3/12; C25F 7/00; C12M 25/14; C25D 11/32
See application file for complete search history.

(56) References Cited

U.S. PATENT DOCUMENTS 5,348,627 A 9/1994 Propst et al.
9,738,860 B2 * 8/2017 Vacanti .................. C12M 25/02
(Continued)

FOREIGN PATENT DOCUMENTS

WO 2019050947 A1 3/2019

OTHER PUBLICATIONS

Ouyang et al., âPhotochemical etching of silicon by two photon absorption, â Phys. Stat. Sol. (A) 204, No. 5, 1255-259 (2007) (Year: 2007).*
(Continued)

*Primary Examiner* — Brian W Cohen
(74) *Attorney, Agent, or Firm* — CALFEE, HALTER & GRISWOLD LLP

(57) ABSTRACT

Three-dimensional scaffolds to facilitate engineered tissue growth are described herein. An exemplary scaffold comprises a first capillary element, a second capillary element, and a connective element that spans a distance between the first capillary element and the second capillary element, connecting the capillary elements. Tissues can be grown within the scaffold such that the tissues have highly vascularized structures with many capillaries running throughout. The scaffolds can be fabricated by selective electrochemical etching of a semiconductor element. The electrochemical etching can be controlled by way of a laser configured to stimulate multiphoton absorption in the semiconductor.

17 Claims, 15 Drawing Sheets

(51) Int. Cl.

| | |
|---|---|
| *B23K 26/362* | (2014.01) |
| *B23K 26/402* | (2014.01) |
| *C12M 1/12* | (2006.01) |
| *C12N 5/071* | (2010.01) |
| *C25F 3/12* | (2006.01) |
| *C25F 7/00* | (2006.01) |

(52) U.S. Cl.

CPC ........... *B23K 26/402* (2013.01); *C12M 25/14* (2013.01); *C12N 5/0692* (2013.01); *C25F 3/12* (2013.01); *C25F 7/00* (2013.01); *C12N 2513/00* (2013.01)

(56) References Cited

U.S. PATENT DOCUMENTS

| | | | | |
|---|---|---|---|---|
| 11,421,338 | B2 * | 8/2022 | Nielson | ............... H01L 21/3063 |
| 2012/0145553 | A1 * | 6/2012 | Kramer | ................. C25D 21/04 |
| | | | | 204/278 |

OTHER PUBLICATIONS

"International Search Report for PCT Patent Application No. PCT/US2018/049543", Mailed Date: Nov. 8, 2018, 2 Pages.

"Written Opinion of the International Searching Authority for PCT Patent Application No. PCT/US2018/049543", Mailed Date: Nov. 8, 2018, 6 Pages.

Bruzauskaite, et al., "Scaffolds and cells for tissue regeneration: different scaffold pore sizes—different cell effects", In Cytotechnology, 2016, pp. 355-369.

* cited by examiner

500

502 — BEGIN

CONTROL ELECTROCHEMICAL
ETCHING OF A SEMICONDUCTOR
BY WAY OF A LASER THAT EMITS
LIGHT HAVING AN ENERGY BELOW
A BANDGAP ENERGY OF THE
SEMICONDUCTOR TO
MANUFACTURE A SCAFFOLD

504

INTRODUCE A TISSUE SAMPLE INTO
A FIRST CAPILLARY ELEMENT OF
THE SCAFFOLD

506

END

508

1400

BEGIN — 1402

APPLY A VOLTAGE BETWEEN A
FIRST SURFACE OF A
SEMICONDUCTOR AND A SECOND
SURFACE OF THE SEMICONDUCTOR — 1404

ILLUMINATE THE SEMICONDUCTOR
AT A FIRST LOCATION BY WAY OF A
LASER HAVING AN ENERGY BELOW
A BANDGAP ENERGY OF THE
SEMICONDUCTOR — 1406

END — 1408

THREE-DIMENSIONAL SILICON SCAFFOLD FOR TISSUE ENGINEERING

RELATED APPLICATIONS

This application claims priority to U.S. Provisional Patent Application No. 62/554,488 filed on Sep. 5, 2017 and entitled "3D SILICON SCAFFOLD FOR TISSUE ENGINEERING," and to U.S. Provisional Patent Application No. 62/618,205 filed on Jan. 17, 2018 and entitled "THREE-DIMENSIONAL SEMICONDUCTOR FABRICATION" the entireties of which are incorporated herein by reference.

BACKGROUND

Engineered tissue growth has been proposed for generating tissues that can be used in testing of pharmaceuticals or other medical treatments, or that can be transplanted into the body of a patient to replace damaged tissue or organs. Artificial scaffolds and other structures have been created to promote cellular growth in engineered tissues. For instance, endothelial culture growth has been demonstrated on thin, porous silicon membranes. However, these thin membranes are unsuitable for growing tissues with vascularity to enable nutrient transport in the tissue. Tissues created on such membranes must themselves be thin in order to allow nutrients to diffuse into the tissue. Other experiments have demonstrated three-dimensional (3D) scaffolds made from photoactive polymers. However, these three-dimensional polymer structures are structurally weak, are limited to relatively large feature sizes (e.g., greater than 100 nanometers in size), and may present biocompatibility problems if implanted in a patient.

SUMMARY

The following is a brief summary of subject matter that is described in greater detail herein. This summary is not intended to be limiting as to the scope of the claims.

Technologies pertaining to engineered tissue growth are described herein. With more particularity, three-dimensional scaffolds are described herein that are suitable for use in connection with growing vascularized tissues. The scaffolds described herein are enabled by the selective electrochemical etching technologies described below, which are able to selectively etch semiconductors (e.g., silicon) to have features less than 100 nanometers in size. In an exemplary embodiment, a 3D scaffold comprises a plurality of capillary elements, and a plurality of connective elements that each span between a pair of capillary elements. An exemplary 3D scaffold can additionally comprise a second plurality of connective elements that span between other connective elements, such that space between capillary elements in the 3D scaffold is at least partially occupied by a web-like arrangement of connective elements.

A tissue can be grown in the 3D scaffold by introducing one or more cellular cultures into the 3D scaffold. Subsequently, a nutrient solution can be pumped through the capillary elements in similar fashion to how blood is pumped through vasculature in tissues in the human body. In an exemplary embodiment, the 3D scaffold can further include an arteriole element and a venule element, wherein the capillary elements of the 3D scaffold are connected between the arteriole element and the venule element. In the example, the nutrient solution can be pumped into the capillary elements by way of the arteriole element and the nutrient solution can be pumped out of the capillary elements by way of the venule element. The nutrient solution provides nutrients to the cellular cultures introduced in the scaffold, and promotes further cell growth throughout the scaffold. Gradually, cells populate the scaffold, adhering to surfaces of the scaffold.

In various embodiments, a 3D scaffold can be manufactured from a single piece of bulk semiconductor material such that the 3D scaffold is of a monolithic construction. The 3D scaffold can be manufactured from silicon. When a tissue is grown in the silicon 3D scaffold, the silicon is gradually resorbed by the tissue. By growing the tissue in the silicon 3D scaffold, a vascularized tissue can be grown wherein no remnant of the scaffold is ultimately left behind in the tissue.

In some embodiments, selective electrochemical etching of a semiconductor is performed based upon a computer-aided design (CAD) model that is representative of a tissue that is desirably replicated. By way of example, a magnetic resonance imaging (MRI) scan or other suitable type of scan of a body of a patient is performed, wherein the scan is indicative of a structure of tissue in the body of the patient (e.g., an organ). For example, the scan may be indicative of a structure of vasculature in the tissue such as positions, size, and orientations of capillaries in the tissue, or a structure of an extracellular matrix of the tissue. Continuing the example, a CAD model can be generated based upon the scan, wherein the CAD model is representative of the structure of the tissue. Selective electrochemical etching of a semiconductor element is then controlled based upon the CAD model to generate a 3D scaffold, as described in greater detail below. A resulting 3D scaffold is therefore substantially similar to the tissue of the patient represented in the scan. A tissue can then be grown in the scaffold, wherein the grown tissue is substantially similar to the tissue represented in the scan of the body of the patient. The tissue thusly grown is more likely to be successfully implanted in a patient by virtue of matching an existing tissue structure of the patient.

Various technologies pertaining to fabrication of structures in a semiconductor by way of selective etching of the semiconductor are also described herein. These technologies are suitable for manufacturing a variety of three-dimensional (3D) structures in a semiconductor (e.g., three-dimensional voids). Furthermore, these technologies are suitable for etching structures in a semiconductor with smaller feature sizes than are typically possible with conventional selective etching techniques. The selective semiconductor etching technologies described herein can be used to fabricate three-dimensional scaffold structures In various exemplary embodiments, a semiconductor is etched by way of electrochemical reactions at a surface of the semiconductor that is exposed to an etchant solution. The exposed surface of the semiconductor is etched selectively based upon controlled creation of holes in the atomic lattice of the semiconductor (i.e., absences of electrons in the lattice that are commonly modeled as positively-charged particles called holes). In the etching reaction, holes at the exposed surface of the semiconductor cause oxidation of the semiconductor, which oxidation is subsequently etched by the etchant solution. Holes are selectively created by illumination of the semiconductor by an illumination source (e.g., a laser) that has an energy below the bandgap energy of the semiconductor. Single sub-bandgap energy photons do not have sufficient energy to move electrons in the semiconductor from the valence band to the conduction band. Thus, ordinarily sub-bandgap energy light is unable to create holes in the atomic lattice of the semiconductor. The sub-bandgap energy light emitted by the illumination source is focused to a sufficiently intense focal spot to cause multi-photon absorption (MPA) within the semiconductor. When this occurs, the photon energy of multiple photons is combined to exceed the bandgap energy of the semiconductor, exciting electrons from the valence band to the conduction band and thereby creating holes in the atomic lattice of the semiconductor at the focal spot of the illumination source. Holes can be selectively created in a region near the focal spot of the illumination source where etching is desirably performed, thereby limiting the etching to a region near the focal spot.

Since the light emitted by the illumination source is sub-bandgap-energy light that does not experience linear absorption, the semiconductor is transparent to the light emitted by the illumination source. By moving the focal spot of the illumination source within the body of the semiconductor, etching of the semiconductor can be selectively controlled to occur at positions that cannot be etched according to conventional semiconductor etching methods. Three-dimensional features can therefore be etched within the body of the semiconductor that are not readily created by conventional microfabrication techniques. In an exemplary embodiment, the illumination source can be positioned facing a second surface (e.g., a backside surface) of the semiconductor opposite the surface exposed to the etchant solution. In the embodiment, the illumination source emits light toward the second surface of the semiconductor and through the semiconductor to the focal spot within the semiconductor body. Illumination of the semiconductor through the second surface opposite the etching surface avoids potential scattering of the emitted light, which can cause undesired etching of the semiconductor or can lower achievable resolution of semiconductor features.

In other exemplary embodiments, the illumination source is controlled by way of a computing device that incorporates a physics model of charge-carrier transport within the semiconductor. In general, a hole generated at a first location in a semiconductor can move within the semiconductor subject to various forces caused by electric fields, carrier diffusion etc. In some instances, therefore, holes created at the first location in the semiconductor may move to a location in the semiconductor other than a location that is desirably etched. By incorporating a physics model of charge-carrier transport, the computing device can control the illumination source such that holes are created by the emitted light at locations where they will ultimately migrate to desired etching locations. By way of example, the computing device is provided with a desired etch location in the semiconductor. The computing device outputs a prediction based upon the physics model, where the prediction indicates that a hole created at a first location is expected to migrate to the desired etch location. The physics model can output the prediction based upon charge-carrier diffusion in the semiconductor, an electric field applied to the semiconductor (e.g., by way of a bias voltage), and a current flow in the electrochemical cell that drives the etching reaction. The computing device then controls the output of the illumination source to cause the illumination source to illuminate the semiconductor with its focal spot at the first location predicted by the physics model.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
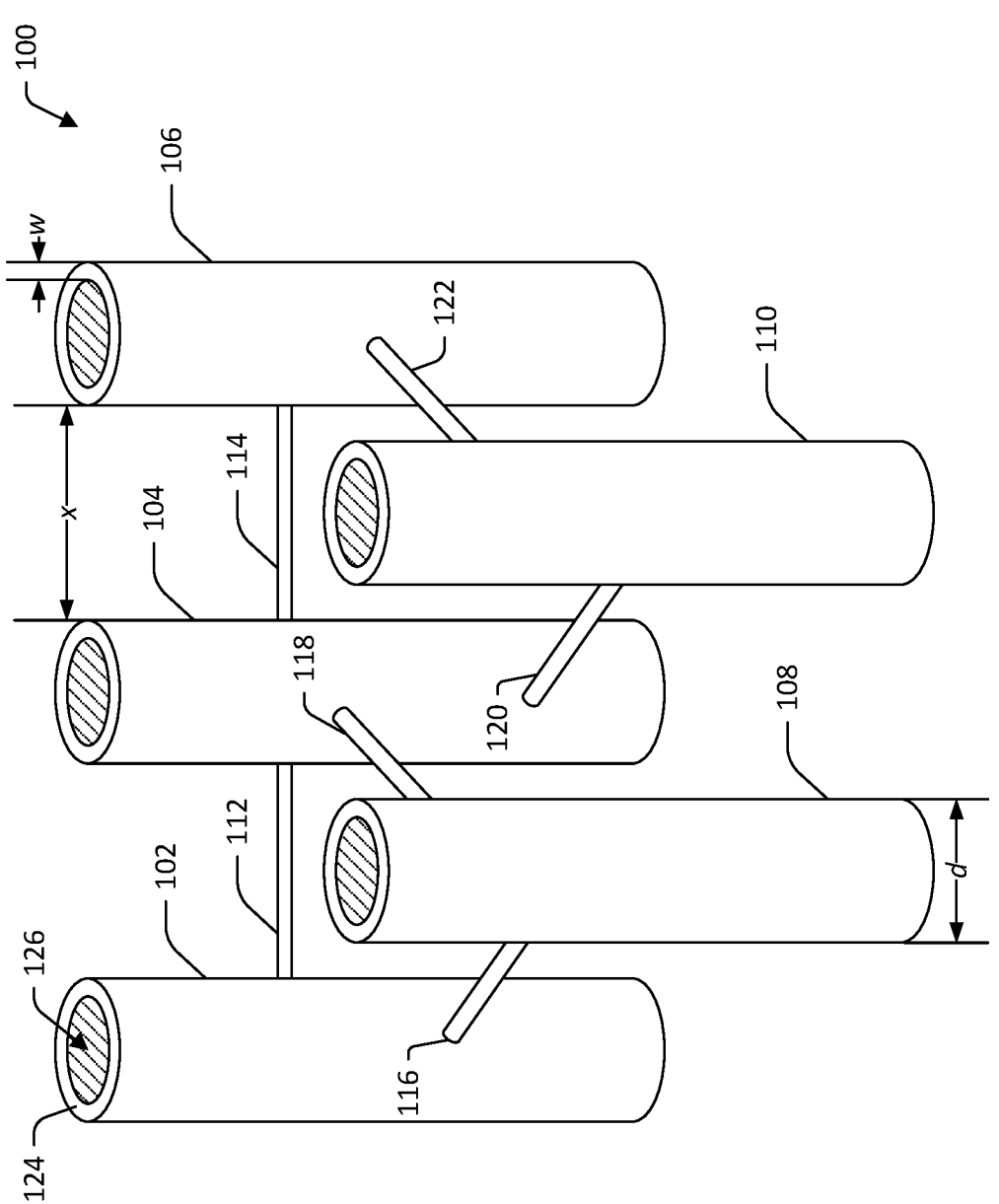
FIG. 1 is a perspective view of an exemplary 3D scaffold for growing tissues.

Various technologies pertaining to 3D scaffolds for facilitating tissue growth and that can be manufactured by photo-controlled selective semiconductor etching are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Additionally, as used herein, the term "exemplary" is intended to mean serving as an illustration or example of something, and is not intended to indicate a preference.

It is to be understood that as used herein, a "hole" in a semiconductor lattice refers to the absence of an electron at a location in the semiconductor lattice. While reference is made herein to various acts and occurrences relative to holes as tangible entities, it is to be understood that such explanation is merely intended to facilitate understanding of various aspects, and may reflect some inaccuracy in an underlying physical process. For instance, while reference is made herein to electric fields exerting forces on holes and causing hole motion, it is to be understood that electric fields actually exert forces on electrons in a semiconductor lattice thereby causing electron motion, whereas results of such motion may be suitably described by conceptualizing a hole as a virtual particle. Such references to holes are made in order to facilitate understanding, and are consistent with descriptions commonly employed in the art of semiconductor fabrication.

Referring now to FIG. 1, an exemplary 3D scaffold 100 that is usable to facilitate tissue growth is illustrated. The scaffold 100 comprises a plurality of capillary elements 102-110 and a plurality of connective elements 112-122. The capillary elements 102-110 are substantially tubular. By way of example, the capillary 102 comprises a wall 124 that defines a hollow interior portion 126 of the capillary 102. The capillaries 102-110 depicted in FIG. 1 are cylindrical, but it is to be understood that the capillaries can be of substantially any tubular shape. For example, in other embodiments the capillaries could be square-shaped tubes. The capillaries 102-110 are configured to carry a fluid (e.g., in the interior portion 126 of the capillary 102). The fluid comprises one or more nutrients to facilitate growth of a tissue in the scaffold 100. The connective elements 112-122 are configured to connect the capillaries 102-110 to one another. The connective elements 112-122 approximate a structure of an extracellular matrix (ECM) that is present in tissues. In general, the connective elements 112-122 are not in fluid communication with the interiors of the capillaries 102-110, and the connective elements 112-122 generally do not carry fluid. In an example, the connective elements 112-122 are comprised of a solid semiconductor material.

In connection with growing a tissue in the scaffold 100, a tissue sample can be introduced into the scaffold 100. By way of example, and not limitation, the tissue sample can be introduced into the interior portion of one of the capillaries 102-110. In the example, the tissue sample adheres to the interior of the wall of the capillary and begins to grow along the wall. The tissue continues to grow in a form substantially defined by the scaffold 100 such that the tissue forms capillaries within the capillary elements 102-110. In exemplary embodiments the tissue sample introduced into the scaffold 100 can include endothelial cells for growth of capillaries in the capillary elements 102-110, stem cells, or other type of cells. The connective elements 112-122 provide an artificial ECM that provides physical support of the scaffold 100 and tissues as they grow within the scaffold. Ultimately, as a tissue grows in the scaffold 100, the artificial ECM defined by the connective elements 112-122 is replaced by an organic ECM of the tissues themselves. A fluid containing one or more nutrients (e.g., a liquid in which nutrients are suspended) can be pumped through the scaffold 100 to provide nutrients to tissues growing in the scaffold 100.

In one embodiment, tissue samples are introduced into the capillary elements 102-110 of the scaffold, and capillary tissues are fully grown (e.g., where the scaffold 100 is made of silicon, such that all of the silicon of the capillary elements 102-110 is resorbed by the capillary tissues) prior to introducing an additional tissue such as a tissue for growth of an organ into the scaffold 100. In another embodiment, tissue samples are introduced into the capillary elements 102-110 and into interstitial space between the capillary elements 102-110 while the tissues in the capillary elements 102-110 are growing. Hence, an organ or other tissue can begin growing in the scaffold 100 while a capillary bed (e.g., as defined by the arrangement of the capillary elements 102-110) is being grown in the scaffold 100.

The capillaries 102-110 can be sized and positioned to promote growth of a tissue in the scaffold 100. For instance, a diameter d of a capillary, a wall width w of a capillary, and a distance x between capillaries can be selected to approximate dimensions commonly seen in human vascular tissues. In exemplary embodiments, a distance x between capillaries is less than 100 microns, less than 75 microns, or less than 50 microns. A distance x between the capillaries 102-110 that is less than approximately 100 microns can facilitate tissue growth in part because at greater distances nutrients present in the capillaries 102-110 may not readily diffuse through tissues (e.g., such as may be growing in interstitial space between the capillaries 102-110) in concentrations sufficient to support growth of the tissues. It is to be understood, however, that in some applications a distance x between the capillaries 102-110 that is greater than 100 microns may be desirable. In other exemplary embodiments, a diameter d of the capillaries 102-110 is less than 25 microns, between 1 micron and 25 microns, between 5 microns and 20 microns, or between 5 microns and 10 microns. In still other exemplary embodiments, a wall width w of the capillaries 102-110 is less than 2 microns, between 0.5 microns and 2 microns, or between 1 micron and 2 microns. The capillaries 102-110 can be uniformly sized or can be of different sizes. In some embodiments wherein the scaffold 100 is made of silicon, a wall width w of the capillaries 102-110 is selected based upon a desired time for resorption of the silicon by the tissues growing in the scaffold 100.

In various embodiments, capillaries of a scaffold for facilitating tissue growth can be arranged in a regular geometric pattern (e.g., as shown in the arrangement of the capillaries 102-110 in FIG. 1). For example, a regular geometric arrangement of the capillaries can facilitate rapid fabrication of the scaffold. In other embodiments, the capillaries of a scaffold for facilitating tissue growth can be arranged according to a CAD model that is representative of a vascular structure in the body of a patient, as described in greater detail below.

Figure 2:
FIG. 2 is a diagram of various exemplary capillary elements.

In any of the embodiments of a scaffold for facilitating tissue growth that are described herein, different structures of a capillary elements can be used based upon desired behavior of a tissue grown in the capillary. By way of example, and referring now to FIG. 2, three exemplary capillary structures 200-204 are shown, wherein each of the structures 200-204 exhibits different material transport characteristics and encourages the development of tissues with similar transport characteristics. The first capillary structure 200 comprises a wall 206 having an outer surface 208 and an inner surface 210, wherein the wall 206 defines an interior portion 212 of the capillary structure 200. The wall 206 is continuous and nonporous, such that substantially no fluid passes from the interior portion 212 of the structure 200 to the exterior. Endothelial cells growing in the capillary structure 200 form continuous capillaries that allow only small molecules such as water to pass through intercellular clefts. The second capillary structure 202 is a fenestrated structure that comprises a wall 214 that defines an interior portion 216 of the structure 202, wherein a plurality of pores 218 are formed in the wall 214. The pores 218 are small holes (e.g., less than 100 nanometers in diameter, or 10-100 nanometers in diameter) through which small molecules and some proteins are able to diffuse. The structure 202 promotes growth of cells within the structure 202 such that endothelial cells growing in the capillary structure 202 form pores of similar size to the pores 218. The third capillary structure 204 is a discontinuous capillary structure that comprises a wall 220 that defines an inner portion 222 of the structure 204, wherein a plurality of holes 224 are formed in the wall 220. The holes 224 are large relative to the pores 218 of the fenestrated structure 202. In exemplary embodiments, the holes 224 are between 5 microns and 80 microns in diameter. The holes 224 are sufficiently large to allow passage of red and white blood cells. The discontinuous capillary structure 204 promotes growth of endothelial cells within the structure 204 such that there are gaps between the endothelial cells, wherein the gaps are of similar size to the holes 224 in the wall 220 of the structure 204.

Figure 3:
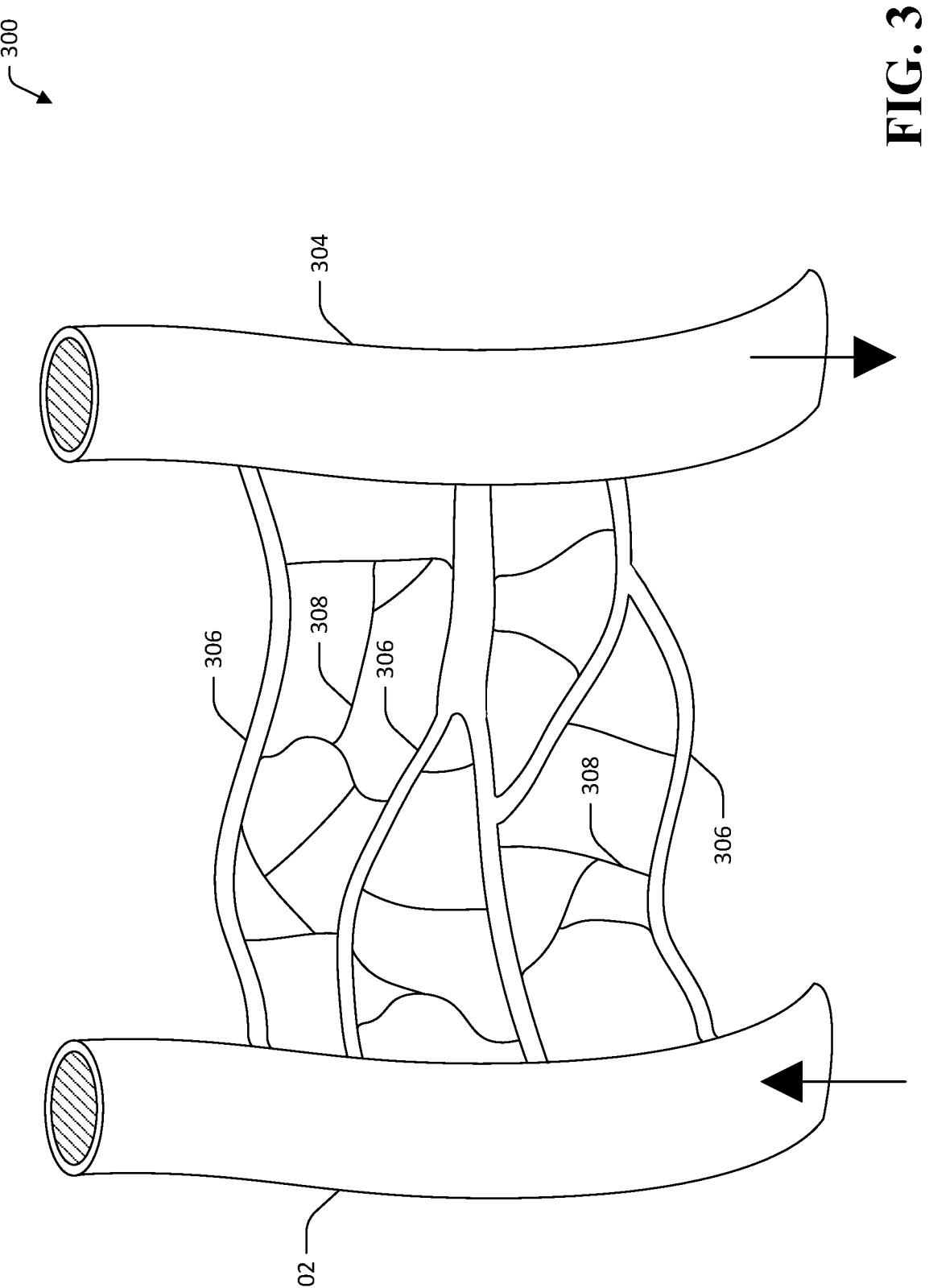
FIG. 3 is a diagram of an exemplary capillary bed that includes an arteriole element and a venule element.

As noted above, a scaffold to facilitate tissue growth can have a non-regular arrangement of capillary elements and connective elements between the capillary elements. A scaffold can also include additional structures that facilitate the provision of nutrients to and provide structural support for the capillary elements. Referring now to FIG. 3, an exemplary scaffold 300 for facilitating tissue growth is illustrated, wherein the scaffold comprises an arteriole element 302, a venule element 304, a plurality of capillaries 306, and a plurality of connective elements 308. The capillaries 306 are connected between the arteriole element 302 and the venule element 304 such that the capillaries 306 are in fluid communication with both the arteriole 302 and the venule 304 (and thus the arteriole 302 is in fluid communication with the venule 304 by way of the capillaries 306). A fluid to supply nutrients to cells growing in the capillary elements 306 can be delivered by way of the arteriole element 302. Once a capillary system has been grown in the capillary elements 306, tissues in the interstitial spaces between the capillary elements 306 (such as organ tissue) can be supplied with nutrients by way of the arteriole 302 and the venule 304. A fluid comprising a nutrient can be pumped into the arteriole element 302 whereupon the fluid enters the capillaries 306. The fluid flows through the capillaries 306 and then into the venule element 304, whereupon the fluid exits the scaffold 304. If the capillaries 306 contain small holes, as in the fenestrated structure 202, or larger holes, as in the capillary structure 204, nutrients can be provided to tissues growing in the interstitial spaces between the capillary elements 206 even before the biological capillary tissues are grown and functional. The fenestrated or discontinuous silicon capillary structures 202 or 204 provide the ability for nutrients to be delivered outside of the capillary structures and for waste products to be absorbed into the fluid in the capillary structures.

In an exemplary embodiment, endothelial cells are grown in the arteriole element 302, the capillary elements 306, and the venule element 304 to create a vascular system having substantially similar structure to the elements 302-306. Stated differently, a vascular system is created that has a biological arteriole that is substantially similar to the arteriole element 302, a plurality of biological capillaries that are substantially similar to the capillary elements 306, and a biological venule that is substantially similar to the venule element 304. A tissue growing in interstitial space between the capillaries can be supplied with nutrients by pumping a nutrient solution into the arteriole, through the capillaries, and out of the venule, in substantially similar fashion to how blood flows through arterioles, capillaries, and venules in naturally occurring tissues.

Further, as can be observed in FIG. 3, the capillaries 306 can diverge from one another or join one another as the capillaries 306 extend from the arteriole 302 to the venule 304. Additionally, the connective elements 308 can connect one of the capillaries 306 to another, can connect one of the connective elements 308 to another, can connect the arteriole 302 or the venule 304 to one of the capillaries 306, etc. The connective elements 308 provide an artificial ECM that can ultimately be supplanted and resorbed by a biological ECM. Hence, the connective elements 308 can be arranged to have a web-like structure similar to a biological ECM. In other embodiments, a pattern of the connective elements can be generated by a mesh generation algorithm that generates a mesh to occupy interstitial space in the scaffold 304 based upon positions and arrangement of the capillaries 306 and the biomechanical needs of the desired tissue cells to be grown in the interstitial space between the capillaries. The biomechanical structure provided by the connective elements 308 can thus influence stem cells to differentiate into the desired tissue type by the stimulus of the artificially created biomechanical spacing of the connective elements 308. The connective elements 308 can further be arranged to provide tube-like open spaces to introduce cells deep into the volume of the scaffold of the desired tissue type (or stem cells intended to differentiate into the desired tissue type).

Figure 4:
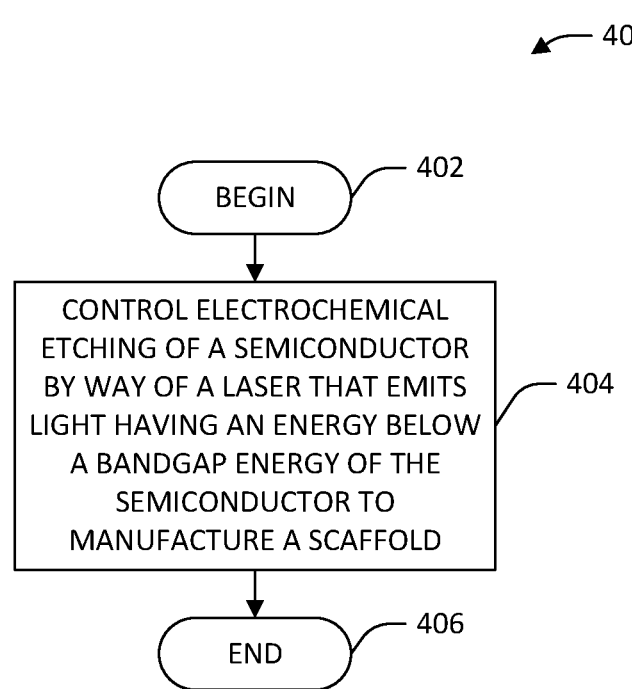
FIG. 4 is a flow diagram that illustrates an exemplary methodology for manufacturing a 3D scaffold for growing tissues.
Figure 5:
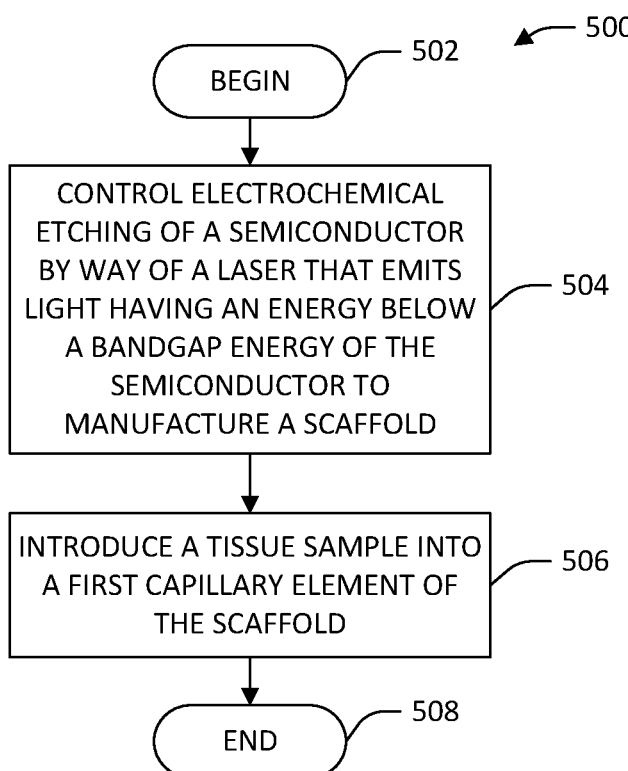
FIG. 5 is a flow diagram that illustrates an exemplary methodology for growing tissues in a silicon scaffold.

FIGS. 4 and 5 illustrate exemplary methodologies relating to fabrication of three dimensional scaffolds and growing vascularized tissues. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Referring now to FIG. 4, an exemplary methodology 400 that facilitates fabricating a three-dimensional scaffold for facilitating growth of a vascularized tissue is illustrated. The methodology 400 begins at 402, and at 404 electrochemical etching of a semiconductor is controlled by way of a laser that emits sub-bandgap-energy light in order to manufacture a scaffold. The electrochemical etching is controlled by the laser such that the scaffold comprises a first capillary element, a second capillary element, and a connective element that spans a distance between the first capillary element and the second capillary element. In an exemplary embodiment, the first and second capillary elements are two of a plurality of additional capillary elements that define a capillary bed.

In further examples, the connective element is one of a plurality of connective elements that define an artificial ECM for a tissue that can be grown in the scaffold. The controlling of the electrochemical etching by way of the laser can proceed according to systems and methods described below with respect to FIGS. 6-15. The methodology 400 completes at 406.

Referring now to FIG. 5, an exemplary methodology 500 that facilitates growing a tissue in a three-dimensional scaffold made up of a semiconductor material is illustrated. The methodology 500 begins at 502 and at 504 electrochemical etching of a semiconductor is controlled by way of a laser to manufacture a scaffold, wherein the laser emits light having an energy below the bandgap energy of the semiconductor. In an example, the electrochemical etching of the semiconductor is controlled by way of the laser such that the scaffold comprises a first capillary element, a second capillary element, and a connective element that spans a distance between the first capillary element and the second capillary element. At 506, a tissue sample is introduced into the first capillary element of the scaffold. The tissue sample can be provided with nutrients by way of the first capillary element of the scaffold, and the tissue thereby encouraged to grow. In an exemplary embodiment, the tissue sample comprises endothelial cells such that the tissue sample introduced at 506 grows to form a capillary having a substantially similar structure to the first capillary element. As the tissue sample continues to grow, the tissue can secrete material to form an ECM along the connective element of the scaffold such that an organic ECM is formed having a substantially similar structure to an artificial ECM defined by the connective element and any other additional connective elements in the scaffold. The methodology 500 completes at 508.

The scaffolds 100, 300 can be manufactured according to systems and methods set forth below with respect to FIGS. 6-15. In exemplary embodiments, the scaffolds 100, 300 are composed of a material that comprises a semiconductor, and the scaffolds 100, 300 are fabricated by selective electrochemical etching of the semiconductor material. By way of example, the scaffold 100 can be selectively etched from a single piece of bulk silicon such that the scaffold 100 is a monolithic structure (e.g., such that the scaffold 100 is a single unitary piece). The selective etching of the silicon can be controlled by a laser that emits light having an energy below the bandgap energy of silicon (e.g., light having a wavelength of greater than approximately 1100 nanometers).

Figure 6:
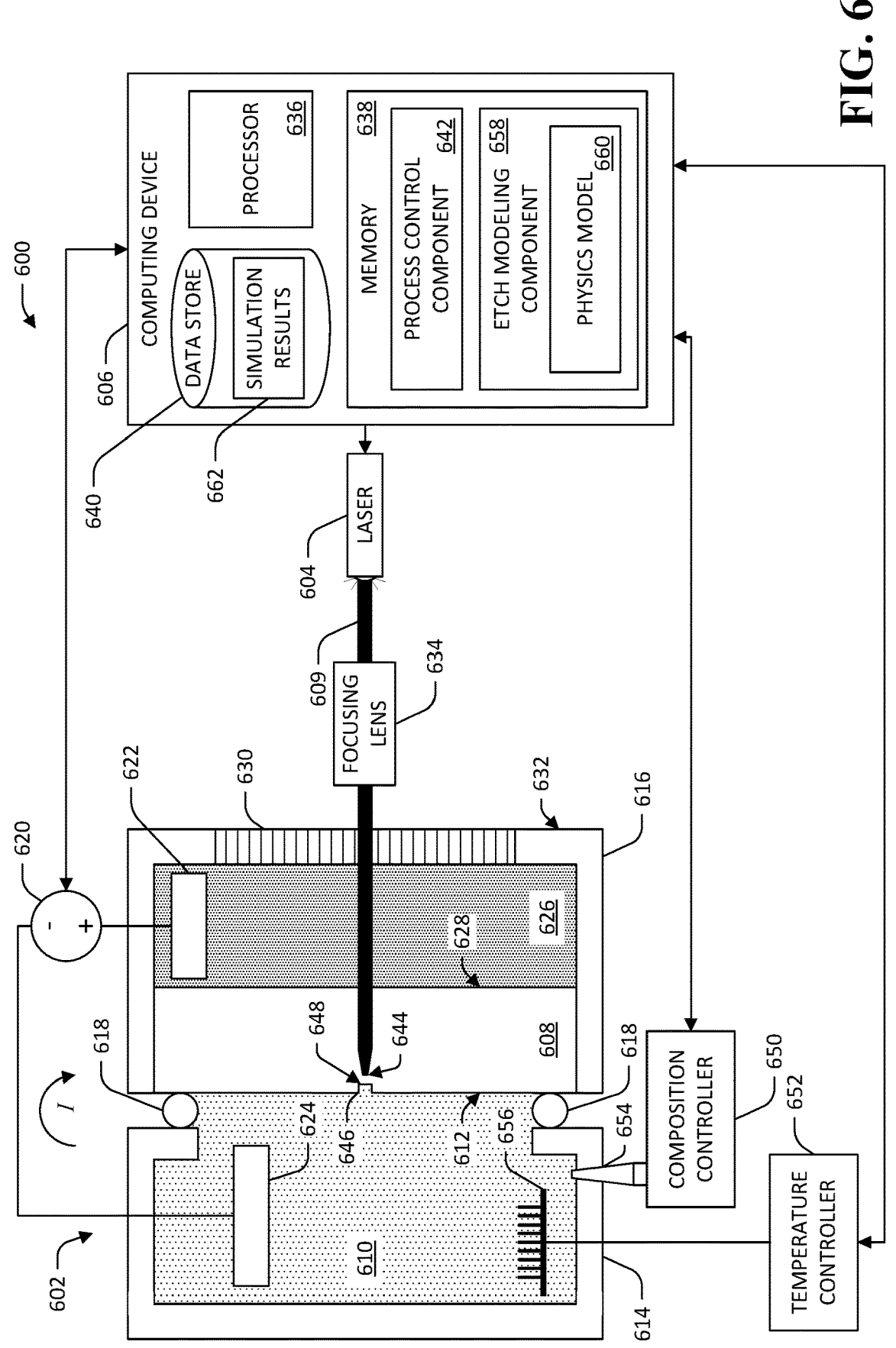
FIG. 6 is a diagram of an exemplary system that facilitates selective etching of a semiconductor controlled by way of a sub-bandgap-energy laser.

Various technologies pertaining to selective electrochemical etching of a semiconductor are now described. With reference to FIG. 6, an exemplary system 600 that facilitates selectively controlled semiconductor etching is illustrated. The system 600 includes an etching chamber 602, a laser 604, and a computing device 606 that controls the laser 604. The etching chamber 602 contains a semiconductor element 608 that is desirably etched and an etching solution 610 that selectively oxidizes and etches the semiconductor 608 at locations where holes exist in the atomic lattice of the semiconductor 608. The laser 604 emits a beam of light 609 at the semiconductor 608 based on control signals received from the computing device 606 in order to create holes at particular regions in the semiconductor 608. The semiconductor 608 is then etched by the etching solution 610 at locations where the created holes migrate to a first surface 612 of the semiconductor 608 that is exposed to the etching solution 610. Hence, the laser 604 is controlled to cause the semiconductor 608 to be etched at desired locations based upon where the laser 604 creates holes in the semiconductor 608.

Composition of the etching solution 610 is selected based upon a chemical makeup of the semiconductor 608. By way of example, and not limitation, in applications where the semiconductor 608 comprises silicon or other carbon group elements (e.g., silicon, carbon, germanium, etc.), the etching solution 610 can comprise hydrofluoric acid (HF). For example, the etching solution 610 can be a solution of between 1% and 30% HF. In other embodiments, other chemicals that provide fluorine atoms for the reaction can also be used, such as ammonium hydroxide/ammonium fluoride. In various embodiments, the etching solution 610 can include surfactants (e.g., ethanol, Dimethylformamide, acetonitrile, etc.) that enhance wetting of the etching solution 610 to the surface 612 of the semiconductor 608 and can facilitate removal of etch gases from the surface 612 of the semiconductor 608. It is to be understood that methods and systems described herein are suitable for selective etching of a variety of semiconductors. In some exemplary embodiments, the semiconductor 608 comprises an intrinsic elemental semiconductor such as silicon, carbon (diamond, graphene, carbon nanotubes, etc.), germanium, etc. In other exemplary embodiments, the semiconductor 608 comprises a group III-V semiconductor (e.g., gallium arsenide, indium phosphide, etc.), a group III-nitride (e.g., gallium nitride, indium gallium nitride, etc.), a group II-VI semiconductor (e.g., zinc oxide, cadmium telluride, etc.) or other semiconductor compounds (e.g., silicon carbide, silicon germanium, etc.). A composition of the etching solution 610 can be selected to facilitate etching of the desirably etched semiconductor. In connection with manufacturing scaffolds to facilitate growth of tissues, the desirably etched semiconductor may be selected based on biocompatibility of the semiconductor with the desirably grown tissues. By way of example, silicon may be selected as a suitable semiconductor for fabricating the scaffolds 100, 300 since endothelial cells are able to adhere to and grow on silicon surfaces and the silicon is able to be resorbed by growing tissues.

Various details pertaining to configuration and operation of the system 600 in connection with selectively etching the semiconductor element 608 are now described. The etching chamber 602 comprises a first containment vessel 614 and a second containment vessel 616. The first containment vessel 614 contains the etching solution 610. The vessels 614, 616 are joined by a seal 618 (e.g., an O-ring, where the vessels 614, 616 are annular) that prevents escape of the etching solution 610 from the etching chamber 602. The semiconductor 608 is positioned in the second containment vessel 616 such that the first surface 612 of the semiconductor 608 is exposed to the etching solution 610.

The system 600 further comprises a voltage source 620 that establishes an electric field in the semiconductor that facilitates the etching reaction at the surface 612 of the semiconductor 608. The voltage source 620 is connected to an anode electrode 622 and a cathode electrode 624 at positive and negative terminals of the voltage source 620, respectively. The anode electrode 622 is positioned within the second containment vessel 616 in contact with a conductive material 626. The conductive material 626 is placed in contact with a second surface 628 of the semiconductor 608 that is opposite the surface 612 that is exposed to the etching solution 610. When a voltage is applied to the electrodes 622, 624 by the voltage source 620, an electric field is established within the semiconductor 608 that can be used to direct charge-carriers to desired locations within the semiconductor 608. For instance, the voltage source 620 can be controlled to establish an electric field within the semiconductor 608 that tends to cause positive charge-carriers, such as holes, to migrate toward the etching surface 612.

The second containment vessel 616 further comprises a window 630 positioned at an outer surface 632 of the vessel 616 and extending through the surface 632 to face the backside surface 628 of the semiconductor 608 (i.e., the surface opposite the surface being etched). The window 630 is transparent to the beam 609 emitted by the laser 604. The laser 604 is positioned facing the window 630 and emits the beam 609 through the window 630 toward the backside 628 of the semiconductor 608. The conductive material 626 is selected or configured to be transparent to the beam of light 609 emitted by the laser 604. By way of example, and not limitation, the conductive material 626 can be salt water, an acid, a base, a transparent conductive oxide, a very thin metal film (e.g., 10-50 nm), a metal mesh, graphene, carbon nanotubes, a transparent conductive polymer, etc. In another exemplary embodiment, the conductive material 626 can be a weak HF solution. Where the etching solution 610 comprises HF, use of a HF solution as the conductive material 626 can inhibit undesired reactions between the etching solution 610 and the conductive material 626 should they come into contact. The system 600 can further include a focusing lens 634 (e.g., an objective lens, or a custom optical focusing element) that receives the beam 609 from the laser 604 and focuses the beam 609 through the window 630 to a focal spot within the semiconductor element 608. The beam 609 would be a focal cone after exiting the focusing lens 634, however, for simplification and illustrative purposes the beam 609 (and in some subsequent figures) is shown as a straight beam until it reaches its focal position 644.

The computing device 606 comprises a processor 636, memory 638 that is operably coupled to the processor 636, and a datastore 640 operably coupled to the processor 636. The memory 638 includes instructions that, when executed by the processor 636 cause the processor 636 to perform various functions. a process control component 642 that controls various aspects of a process for selectively etching the semiconductor 608. For example, the process control component 642 controls orientation and positioning of the laser 604 and/or the focusing lens 634 in connection with illuminating particular locations in the semiconductor 608. The process control component 642 can also be configured to control other etch input variables such as intensity of the beam 609, the bias voltage applied by the voltage source 620, temperature of the etching solution 610, etc.

Operations of the system 600 in connection with selectively etching the semiconductor 608 are now described. Etching of the semiconductor 608 by the etching solution 610 occurs based upon a series of chemical reactions that are carried out at the etching surface 612 of the semiconductor 608 in the presence of holes in the atomic lattice at the surface 612. For example, in an exemplary embodiment wherein the semiconductor 608 comprises silicon and the etching solution 610 comprises hydrofluoric acid, the etching reaction is the following two-step electrochemical reaction:

$$Si+2F^-+2h^+\rightarrow SiF_2 \quad\quad (1)$$

$$SiF_2+2HF\rightarrow SiF_4+H_2 \qu\quad (2)$$

In the chemical reaction shown in Equation 1, positively charge holes at the surface of a silicon semiconductor facilitate a reaction between negatively charged fluorine ions and neutral silicon to yield $SiF_2$ at the surface. The chemical reaction of Equation 2 is the etching reaction, whereby the HF etching solution reacts with the $SiF_2$ to yield $SiF_4$ and $H_2$ gases. The electrochemical etching reaction described by Equations 1 and 2, therefore, can be controlled by controlling a quantity and location of holes in the semiconductor. Where holes are present, etching can occur, and where holes are absent etching does not occur. Other alternative chemical reaction equations have been proposed for silicon electrochemical etching of silicon with an intermediate silicon oxide step. In general, various proposed reaction equations and experimental results demonstrate a need for holes for the etch to occur.

In the exemplary system 600, holes are created by illumination of the semiconductor 608 by the laser 604. Since an electrochemical etching reaction of the etching solution 610 with the semiconductor 608 is facilitated by the presence of holes, etching of the semiconductor 608 can be controlled based upon illumination of the semiconductor 608 by the laser 604. In order to create a hole in a semiconductor, sufficient energy must be imparted to an electron in the lattice of the semiconductor to allow the electron to bridge the bandgap of the semiconductor from the valence band to the conduction band. Conventionally, therefore, holes have been created in semiconductors using a laser wherein each photon has an energy greater than the bandgap energy of the semiconductor.

By contrast, the laser 604 is a laser that emits light wherein the photon energy is less than the bandgap energy of the semiconductor 608. Sub-bandgap-energy light is ordinarily not absorbed by the semiconductor 608, and thus the semiconductor 608 is typically transparent to the beam 609 emitted by the laser 604. The focusing lens 634 is configured to focus the beam 609 to an intense focal spot 644 in the semiconductor 608. Whereas ordinarily sub-bandgap-energy light does not impart sufficient energy to an electron to cause the electron to be freed from its location in the lattice of the semiconductor (thereby creating a hole), when the focusing lens 634 focuses the beam to the intense focal spot 644, MPA can occur whereby multiple photons impart energy to an electron substantially simultaneously. When an electron absorbs multiple photons each having an energy below the bandgap energy, sufficient energy can be imparted to cause the electron to move from the valence band to the conduction band, thereby creating a hole.

Figure 7:
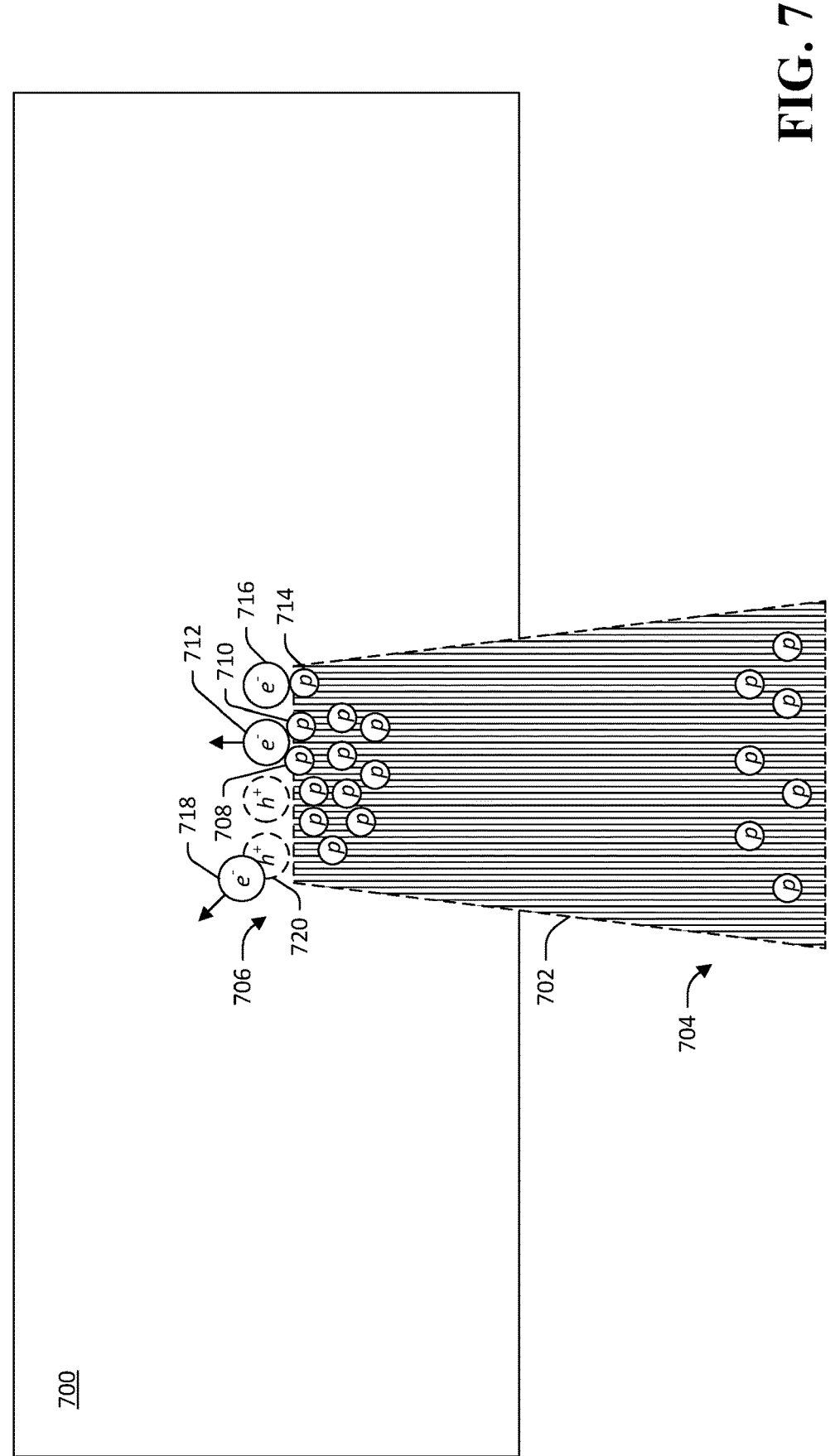
FIG. 7 is a conceptual diagram of MPA in a vicinity of a focal spot of a sub-bandgap-energy illumination source.

By way of illustration, and referring now to FIG. 7, a conceptual diagram of creation of holes in the atomic lattice of a semiconductor is shown. It is to be understood that while certain aspects pertaining to electrons, photons, and holes are depicted and described with respect to FIG. 7, such aspects are intended only as a conceptual illustration to facilitate understanding of an underlying physical process and are not intended as a fully accurate depiction of subatomic physical processes. FIG. 7 depicts a snapshot view of a semiconductor 700 that includes a plurality of electrons $e^-$. The electrons $e^-$ are constrained to be either in the valence band of the semiconductor 700 or the conduction band of the semiconductor 700. FIG. 7 further depicts a beam 702 of light, e.g., as emitted by a laser. As shown in FIG. 7, the beam 702 includes a plurality of photons p, wherein each of the photons p has an energy below the bandgap energy of the semiconductor 700.

Initially, the beam 702 is unfocused in a region 704. In the unfocused region 704, the beam 702 is unlikely to impart sufficient energy to an electron to cause the electron to cross the bandgap from the valence band to the conduction band, as it is unlikely that two or more photons will impart energy to an electron simultaneously. The beam 702 comes into focus at a focal spot 706 within the semiconductor 700. At the focal spot 706, fluence of the beam 702 (i.e., energy per unit area) increases relative to the unfocused region 704. Thus, at the focal spot 706 it is more likely that two or more photons will impart energy to an electron at substantially the same time. MPA occurs at the focal spot 706 of the beam 702. For instance, as shown in FIG. 7, two photons 708, 710 arrive simultaneously at an electron 712. The photons 708, 710 impart sufficient energy to cause the electron 712 to move from its position in the atomic lattice of the semiconductor 700, as indicated by the arrow extending from the electron 712. By contrast, only a single photon 714 arrives at another electron 716 at the snapshot of time depicted in FIG. 7. Since the photons p of the beam 702 have a sub-bandgap energy, the single photon 714 is insufficient to impart enough energy to the electron 716 to cause the electron 716 to move from its position in the lattice and, therefore, photon 714 is not absorbed and electron 716 does not leave the valence band. When an electron e⁻ leaves its position in the lattice of the semiconductor 700 a positively-charged hole h⁺ remains behind. For example, an electron 718 is depicted as moving away from a position in the lattice while a hole 720 remains in its place.

Referring again to FIG. 6, holes are created at the focal spot 644 by MPA of the sub-bandgap-energy light of the beam 609 by electrons in the atomic lattice of the semiconductor 608 at the focal spot 644. Holes created at the focal spot 644 can migrate to the etching surface 612, causing oxidation and subsequent etching of the semiconductor 608 at locations of holes at the surface 612. By way of example, the semiconductor 608 comprises an etched feature 646 that extends into the semiconductor 608 from the surface 612. As holes created at the focal spot 644 migrate to a bottom surface 648 of the etched feature 646, the etching solution 610 oxidizes and etches the bottom surface 648 of the feature 646 to further extend the feature 646 into the body of the semiconductor 608.

The process control component 642 can control various parameters of the electrochemical etching of the semiconductor 608 by the etching solution 610 in the etching chamber 602 to facilitate etching of desired features. In an example, an electrical field can be established and variably controlled to affect a size or shape of a feature etched in the semiconductor 608. In the system 600 the computing device 606 is in communication with the voltage source 620, and the process control system 642 is configured to control an output of the voltage source 620. The process control system 642 can control the voltage source 620 to establish an electric field in the semiconductor 608. The electric field can be maintained such that holes are swept to the etching surface 612, as referenced above. Establishment of the electric field in the semiconductor 608 by way of the voltage source 620 facilitates performance of selective etching of the surface 612 of the semiconductor 608 by directing holes to desired locations in the lattice of the semiconductor. Various internal electric fields (not due to the voltage source 620) within the semiconductor 608 exert forces on holes in the semiconductor 608 that can cause semiconductor drift. Further, holes diffuse through the semiconductor 608 from areas of higher concentration to areas of lower concentration. Establishing an electric field within the semiconductor 608 using the voltage source 620 can reduce an effect of other electric fields and carrier diffusion on an ultimate position of a hole at the surface 612 of the semiconductor 608 by reducing a time between generation of the hole at the focal spot 644 of the laser 604 and the hole reaching the surface 612. In exemplary embodiments, a voltage of less than or equal to about 2 volts (e.g., less than 2 volts) supplied by the voltage source 620 is found to be sufficient to enable feature sizes of less than 100 nanometers as may be desired in various embodiments of the scaffolds 100, 300 described above. Higher voltages may alternatively be used in conjunction with electric field focusing to achieve features with sizes smaller than the optical resolution limit in the semiconductor material.

Figure 8:
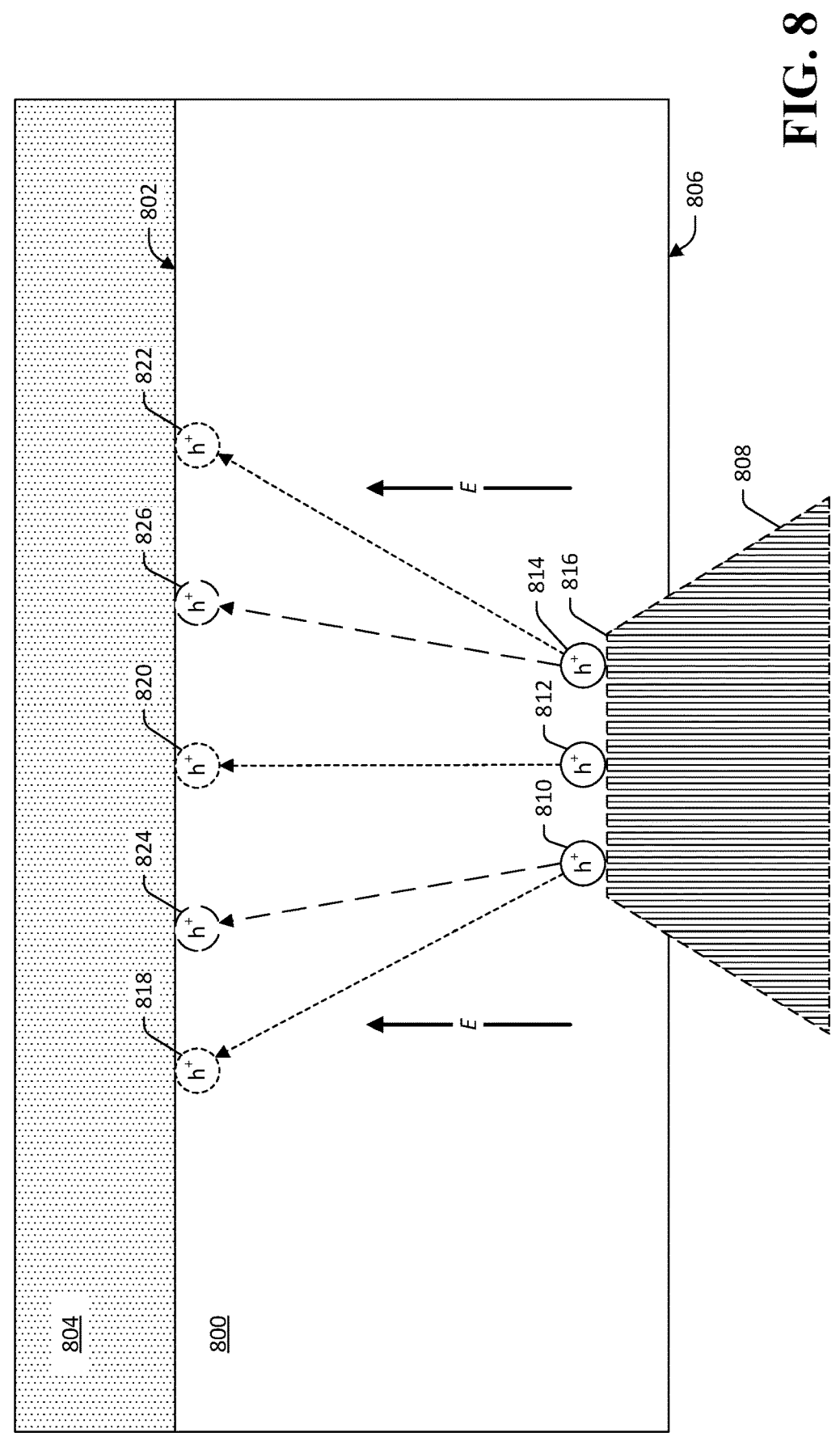
FIG. 8 is a conceptual diagram of hole drift under the influence of induced electric fields.

By way of example, and referring now to FIG. 8, a diagram depicting migration of holes under the influence of two different electric fields is illustrated. FIG. 8 depicts a semiconductor element 800 that comprises a first surface 802 that is exposed to an etching solution 804 and a second surface 806 opposite the first surface 802, wherein a beam of sub-bandgap-energy light 808 enters the semiconductor 800 through the second surface 806. The beam 808 generates a plurality of holes 810-814 at a focal spot 816 of the beam 808 that is positioned within the semiconductor 800. The holes 810-814 migrate toward the etching surface 802 of the semiconductor 800 under the influence of an electric field E. For a first intensity of the electric field E, the holes 810-814 migrate to respective positions 818-822. If the electric field E is increased to a second, greater intensity (e.g., by increasing a voltage output of the voltage source 620 in the system 600), the holes 810-814 may be swept to the etching surface 802 more quickly. As shown in FIG. 8, under the influence of an electric field having the second, greater intensity, the holes 810, 814 migrate to respective positions 824, 826 that are closer together than the positions 818, 822. Therefore, a size (e.g., a diameter) of an etch feature for a given set of illumination parameters (e.g., size, position, intensity of the focal spot of the laser) can be increased by reducing the intensity of the electric field E or can be decreased by increasing the intensity of the electric field E.

Still other parameters of the system 600 can be controlled by the process control component 642 in connection with etching desired features in the semiconductor 608. In an exemplary embodiment, the process control component 642 outputs a control signal to the laser 604 and/or the focusing lens 634 that causes the laser 604 and/or the focusing lens 634 to adjust size, intensity, or positioning of the focal spot 644 within the semiconductor 608 to affect a resultant etch.

Figure 9:
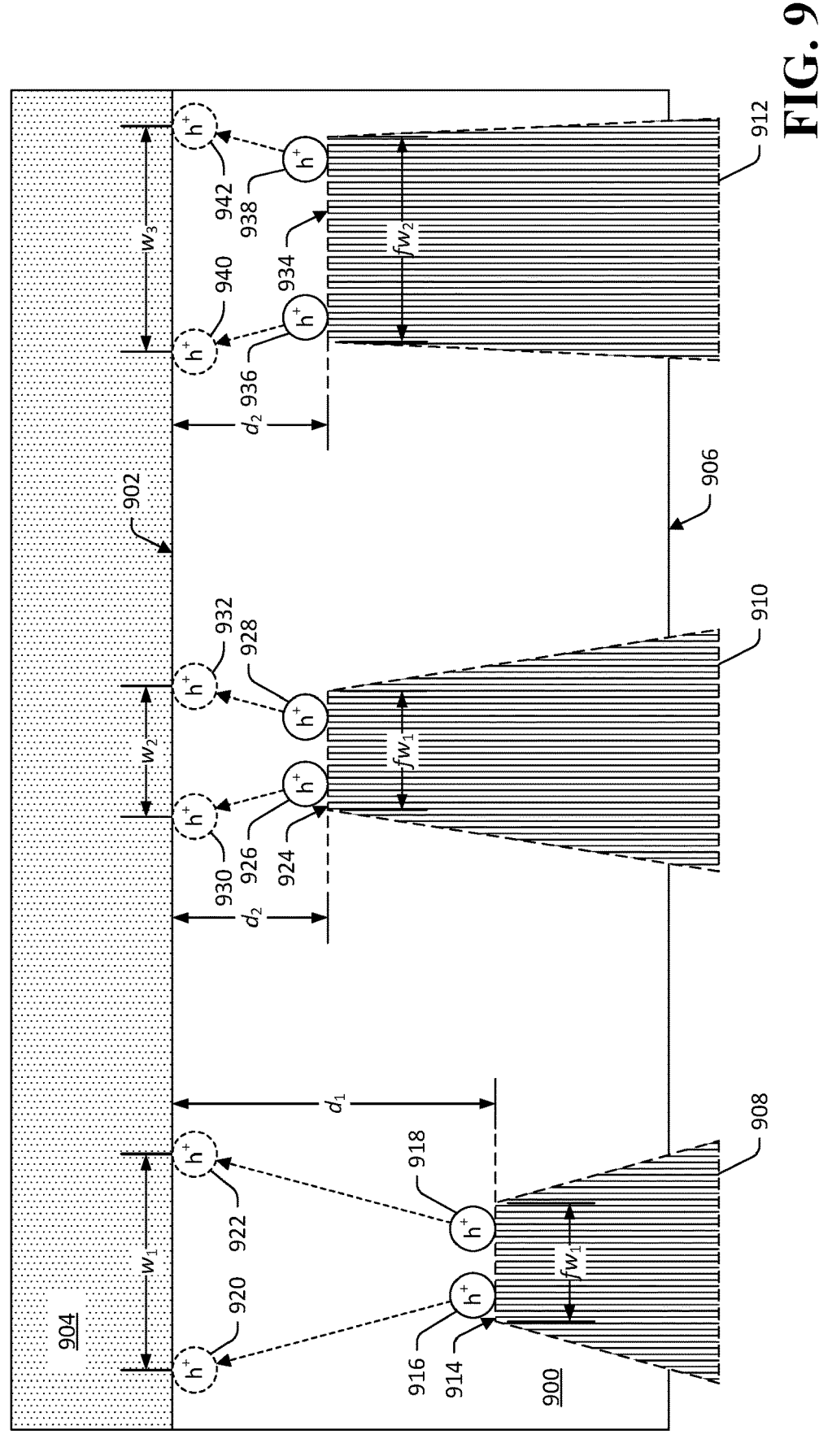
FIG. 9 is a conceptual diagram illustrating generation and migration of holes in a semiconductor.
Figure 10:
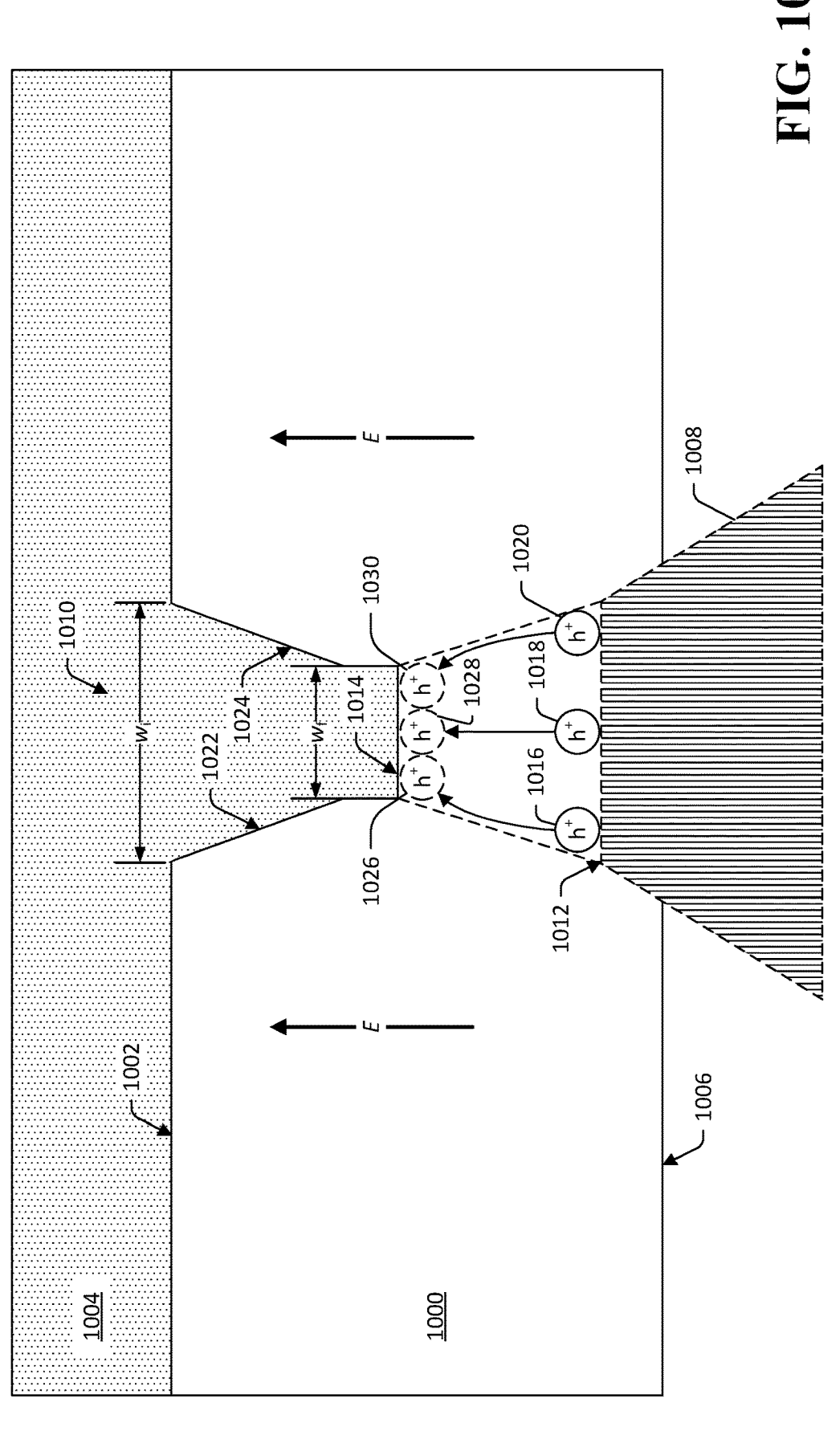
FIG. 10 is a conceptual diagram illustrating electric field focusing effects on migration of holes in a semiconductor.

By way of example, and referring now to FIG. 9 a diagram depicting differences in migration of holes within a semiconductor for various sizes and positions of a focal spot is illustrated. FIG. 9 depicts a semiconductor element 900 that comprises a first surface 902 that is exposed to an etching solution 904 and a second backside surface 906 opposite the first surface 902, wherein beams 908-912 of sub-bandgap-energy light are depicted as entering the semiconductor 900 through the backside surface 906. Each of the beams 908-912 has a different combination of focal spot size and position relative to the etch surface 902. The beam 908 has a focal spot 914 with a focal spot width $fw_1$ positioned at a depth of $d_1$ away from the etching surface 902. Holes 916, 918 are depicted as being initially spaced a maximal distance of $fw_1$ apart at the focal spot 914. Due to carrier diffusion, internal or induced electric fields, or other various forces, the holes 916, 918 migrate to positions 920, 922 at the etch surface 902 of the semiconductor 900. The positions 920, 922 are positioned a width $w_1$ apart, where a value of $w_1$ depends on various etch parameters described herein. Similarly, the beam 910 has a focal spot 924. The focal spot 924 of the beam 910 has the same focal spot width $fw_1$ as the focal spot 914 of the first beam 908, but the focal spot 924 is positioned at a shallower depth $d_2$ than the depth $d_1$ of the first focal spot 914. As a result, all else being equal, holes 926, 928 generated at a maximal distance of $fw_1$ apart at the focal spot 924 migrate to respective second positions 930, 932 at the etching surface 920 that are spaced a smaller width $w_2$ apart than the width $w_1$. For a same-size focal spot, a size of an etch feature at the etch surface of the semiconductor can be increased by increasing a distance between the focal spot and the etch surface.

A width of the focal spot can also affect a width of a resultant etch feature. Still referring to FIG. 9, the third beam 912 has a focal spot 934 positioned at the same depth $d_2$ as the focal spot 924 of the second beam 910. The focal spot 934 of the third beam 912 further has a focal spot width $fw_2$ that is greater than the focal spot width $fw_1$ of the second beam 910. Holes 936, 938 are depicted as being generated at a maximal distance of $fw_2$ apart at the focal spot 934. The holes 936, 938 are shown as migrating to respective second locations 940, 942 at the etch surface 902, the locations 940, 942 spaced a width $w_3$ apart. The width $w_3$ is greater than the width $w_2$ indicating that, all else being equal, the greater focal spot width $fw_2$ yields a greater etch feature width $w_3$.

A position of the focal spot 644 of the laser 604 can further be controlled relative to positions of existing etched features in the semiconductor 608 to affect a resultant size or shape of an etched feature. For example, the focal spot 644 can be positioned in close proximity to a surface of an etched feature in the semiconductor 608 (e.g., within 10 nanometers of the surface of the feature to within 10 to 200-microns of the surface of the feature or more depending on the carrier diffusion length of the specific semiconductor), such that internal electric fields established by the geometry of the etched feature alter motion of holes created at the focal spot 644. In a non-limiting example, and referring now to FIG. 10, a diagram of an exemplary etch of a semiconductor 1000 is shown, wherein holes are generated in close proximity to an existing etch feature to reduce a size of the etching. The semiconductor comprises a frontside surface 1002 that is exposed to an etching solution 1004 and a backside surface 1006 through which a beam of sub-bandgap-energy light 1008 enters the semiconductor 1000. The semiconductor 1000 includes a feature 1010 etched in the surface 1002 of the semiconductor 1000. The feature 1010 has an initial width $w_i$ at the surface 1002. In an exemplary embodiment, the initial width $w_1$ is based on a width of a focal spot 1012 of the beam 1008, an intensity of an induced electric field E in the semiconductor 1000, a relative difference in concentration of charge carriers between the surface 1002 and the location of focal spot 1012, etc. As the feature 1010 extends into the semiconductor 1000, the width of the feature 1010 tapers to a smaller final width $w_f$, due to electric field focusing of charge-carriers at a tip 1014 of the feature 1010.

By way of illustration, a plurality of holes 1016-1020 are generated at the focal spot 1012 of the beam 1008. Under the influence of the induced electric field E, the holes 1016-1020 migrate from the focal spot 1012 of the beam 1008 toward the etching surface 1002 of the semiconductor 1000. In the absence of an existing feature, a smallest width of an etch feature at the surface 1002 may be limited by a focal spot size of the beam 1008. For example, in connection with initially etching the feature 1010 at the surface 1002 of the semiconductor 1000, the initial width $w_1$ may be the width of the focal spot 1012. As the feature 1010 is etched into the semiconductor, surfaces of the feature 1010 (e.g., interior surfaces 1022, 1024) cause the electric field lines (not pictured) to be bent from surface 1006 towards the feature 1010, and in particular towards the tip 1014 of the feature 1010. This change in the electric field due to feature 1010 exert forces on holes as they migrate through the semiconductor 1000. Accordingly, the holes 1016-1020 that are created at the focal spot 1012 of the beam 1008 are drawn toward the tip 1014 of the feature 1010 to positions 1026-1030 within the width $w_f$. Whereas absent the feature 1010 the holes 1016-1020 may spread apart as they migrate toward the surface 1002 (e.g., due to charge-carrier diffusion in the semiconductor 1000), surfaces of the feature 1010 draw the holes toward them In exemplary embodiments, the final width $w_f$ of the feature 1010 is less than the width of the focal spot 1012. Hence, and referring again to FIG. 6, by placing the focal spot 644 of the laser 604 near an etched feature in the semiconductor 608, features can be etched in the semiconductor 608 that have a smaller size than a resolution limit of the laser 604 and focusing lens 634. In one illustrative example, if the laser 604 has a minimum focal spot size of 1000 nanometers, the process control component 642 can control the laser 604 to take advantage of electric field focusing to etch features having dimensions of as little as 10 nanometers.

Since sub-bandgap-energy light is not absorbed by the semiconductor 608 except at the focal spot 644 of the laser 604, the focal spot 644 can be positioned anywhere within the three-dimensional body of the semiconductor 608. This enables etching of three-dimensional features within the semiconductor 608 without requiring a direct straight-line path to the etching surface 612 of the semiconductor 608 as typically required in conventional etching based on photomasks.

Figure 11:
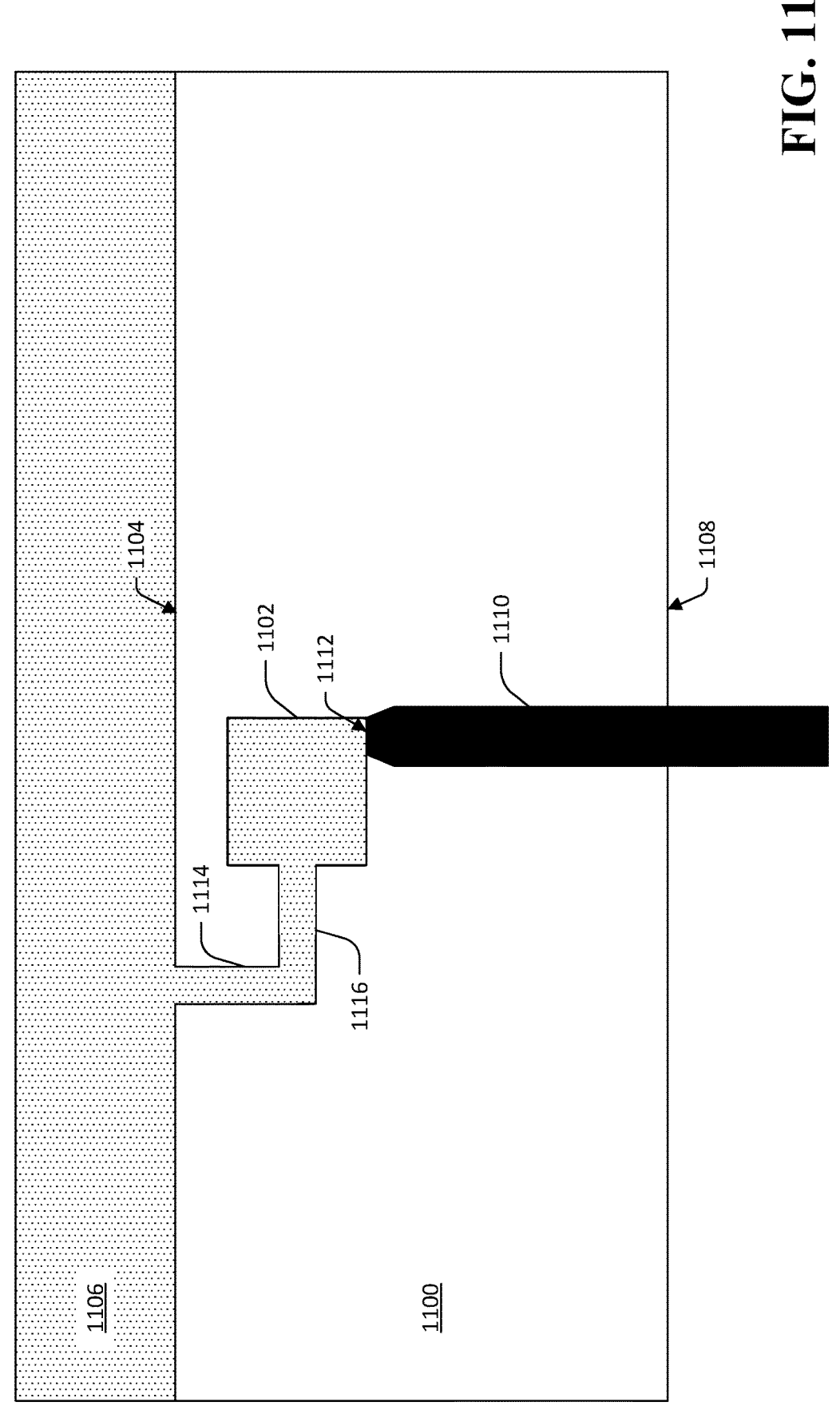
FIG. 11 is a diagram of an exemplary sub-surface semiconductor etch.

For example, and referring now to FIG. 11 an exemplary etching of a semiconductor 1100 is depicted wherein a cavity 1102 is formed within a body of the semiconductor 1100. As shown in FIG. 11, the semiconductor 1100 comprises a frontside surface 1104 that is exposed to an etching solution 1106 and a backside surface 1108 through which a beam 1110 of sub-bandgap-energy light enters the semiconductor 1100. The cavity 1102 is disposed within the bulk of the semiconductor 1100 rather than being formed on a surface of the semiconductor 1100. Since the semiconductor 1100 is transparent to the beam 1108 other than at a focal spot 1112 of the beam 1110, the focal spot 1112 can be positioned to generate holes anywhere within the body of the semiconductor 1100. In connection with etching the cavity 1102, additional channel features 1114, 1116 are etched prior to the etching of the cavity 1102. While a location of etching by the etching solution 1106 can be controlled by controlling generation of holes in the semiconductor 1100 using the beam 1108, in order for a feature to be etched the etching solution 1106 must be able to reach the feature. Hence, the first channel feature 1114 is etched from the frontside surface 1104 and into the bulk of the semiconductor 1100. The second channel feature 1116 is etched subsequent to the first channel feature 1114, as the etching solution 1106 is able to reach the second channel feature 1116 by way of the first channel feature 1114. Subsequently, the cavity 1102 can be etched, as the etching solution 1106 is able to reach the cavity 1102 by way of the previously etched channel features 1114, 1116.

Figure 12:
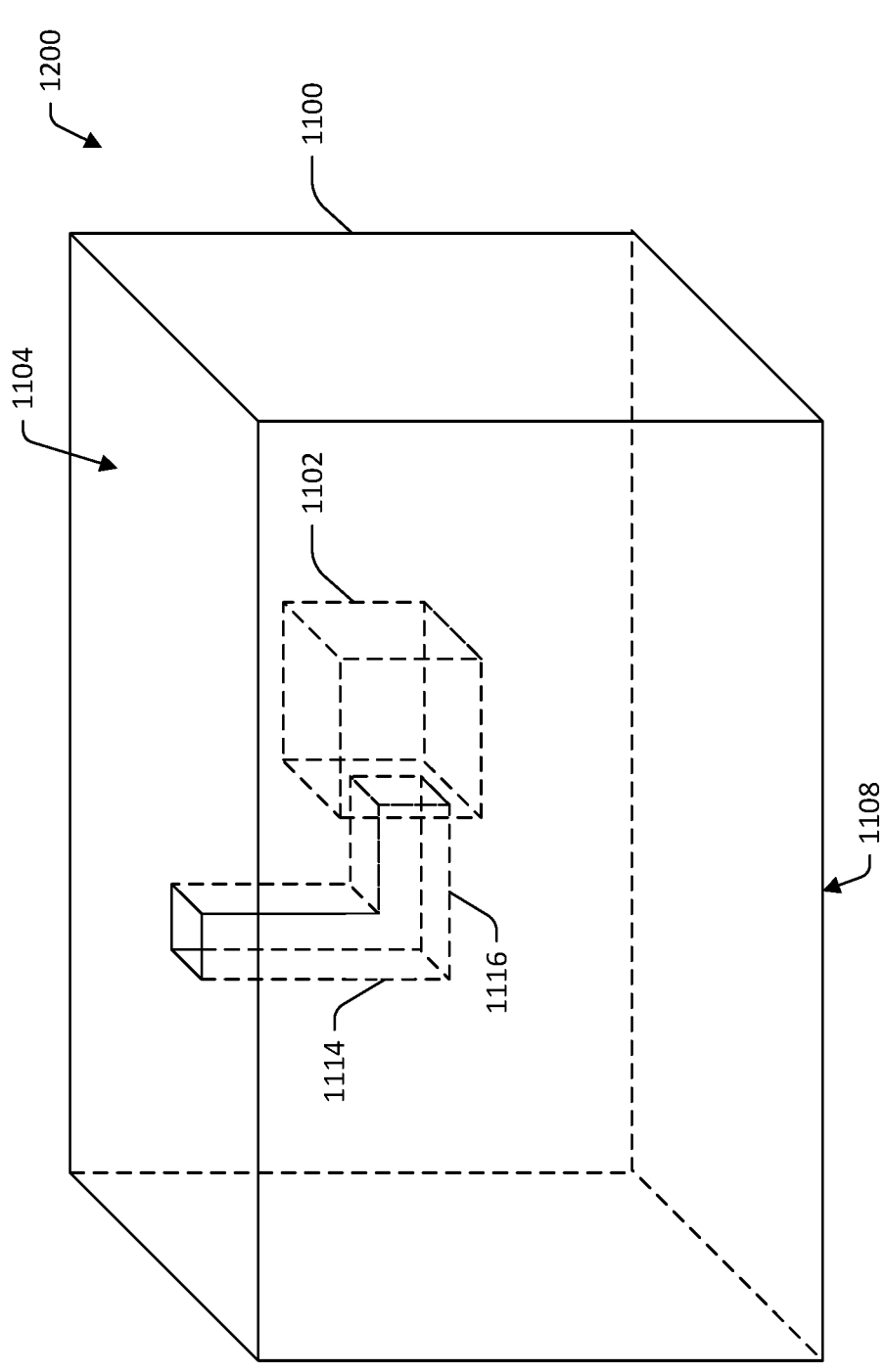
FIG. 12 is a three-dimensional representation of the sub-surface semiconductor etch depicted in FIG. 11.

It is to be understood that while various aspects pertaining to etched features are depicted in the Figures in two-dimensional form to facilitate understanding, the technologies described herein are suitable for etching features of substantially any shape in three dimensions. Referring now to FIG. 12, a three-dimensional representation 1200 of the etched features 1102, 1114, 1116 illustrated in FIG. 11 is shown. In the three-dimensional representation 1200, the semiconductor 1100 is shown to have a rectangular cubic shape. The first channel feature 1114 is a rectangular channel feature extending from the frontside surface 1104 into the body of the semiconductor 1100. The second channel feature 1116 is also a rectangular channel feature and extends horizontally outward from the first channel feature 1114 in the body of the semiconductor 1100. The cavity 1102 is shown to be a cubic cavity that connects with the second channel feature 1116, and thereby is connected to the frontside surface 1104 of the semiconductor 1100 by way of the two channel features 1114, 1116.

Referring once again to FIG. 6, the process control component 642 can further control temperature and composition of the etching solution 610 to maintain desired etch parameters. The system 600 further comprises a composition controller 650 and a temperature controller 652 in communication with the computing device 606. The composition controller 650 is coupled to the interior of the first containment vessel 614 by way of an opening 654 in the containment vessel 614. The composition controller 650 can be controlled by the process control component 642 to remove by-products of the etching reaction from the first containment vessel 614 and/or to introduce additional etching solution to maintain a target composition of the etching solution 610 within the containment vessel 614. In other embodiments, the composition controller 650 can be controlled by the process control component 642 to maintain a desired pressure in the containment vessel 614 in order to prevent the formation of bubbles of gases generated during the etch process. By way of example, gases such as hydrogen or silicon tetrafluoride may be given off during an etch process, and bubbles of such gas can become trapped within a structure being etched into the semiconductor 608. The composition controller 650 can maintain a pressure in the containment vessel 614 to prevent the formation of such bubbles, which can have deleterious effects on the etch process. The temperature controller 652 is coupled to heating/cooling device 656 that is positioned within the containment vessel 614. Responsive to receipt of control signals from the computing device 606, the temperature controller 652 controls the heating/cooling device 656 to heat or cool the etching solution 610 in the containment vessel 614 so as to maintain a target temperature of the etching solution 610 (e.g., as indicated in the control signals transmitted to the temperature controller 652 by the computing device 606).

It is to be understood that any or all of various forces, parameters, and variables described herein may affect migration of holes within the semiconductor 608. It will therefore be the case that holes created at one position may migrate to another position subject to a large number of variable physical parameters (e.g., temperature, voltage between electrodes 622, 624, size, intensity, and position of the focal spot 644, composition of the semiconductor 608, etc.). To facilitate etching of the semiconductor 608 according to a desired etch pattern, the memory 638 includes an etch modeling component 658 that outputs etch control instructions to the process control component 642 based upon an etch definition input to the computing device 606. Furthermore, feedback can be introduced into the control algorithm by monitoring the electrical current I flowing in the electrochemical etch cell (which is related to the rate of etching occurring), monitoring the current temperature of the etching solution 610, monitoring the products resulting from the etch process (e.g., as identified by the composition controller 650), or monitoring an image of the etch front as the etch proceeds.

Exemplary operations of the etch modeling component 658 and process control component 642 in connection with etching the semiconductor 608 according to a desired pattern are now described. An etch definition is provided to the etch modeling component 658, where the etch definition is indicative of position and dimensions of various features desirably etched in the semiconductor 608. Stated differently, the etch definition indicates a plurality of locations at which it is desired (e.g., by an operator of the system 600) that the semiconductor 608 be etched, wherein taken together the plurality of locations define the structure of one or more features to be etched. In exemplary embodiments, the etch definition comprises a computer-aided design (CAD) model that indicates dimensions of a semiconductor and respective positions and dimensions for one or more etch features in the semiconductor. The etch definition input to the etch modeling component 658 can further include one or more desired parameters of the etch. By way of example, and not limitation, the etch definition can include data indicative of a composition of the semiconductor 608, locations of existing etched features in the semiconductor 608, desired operating parameters of the laser 604 and/or the voltage source 620, etc. In connection with etching a scaffold to facilitate growth of a tissue, the etch definition can include a CAD model that is generated based on an MRI or other scan of a portion of a body of a patient. In an example, a scan of a portion of a body of a patient is taken, wherein the scan is indicative of a structure of one or more tissues in the body of the patient. In an illustrative example, the scan can be indicative of sizes, position, and arrangement of capillaries, arterioles, and venules in the body of the patient. A CAD model can be generated from the scan (e.g., by the computing device 606) where the CAD model is representative of the structure of the one or more tissues in the body of the patient. In the example, the CAD model is representative of at least one of a capillary structure or a tissue structure of an organ in the body of the patient. In embodiments, the computing device 606 can then control etching of the semiconductor 608 based upon the CAD model such that the semiconductor 608 is etched to comprise capillary elements, arteriole elements, and venule elements that are substantially similar in structure to capillaries, arterioles, and venules in the body of the patient.

The etch modeling component 658 is configured to output etch control instructions to the process control component 642 based upon the etch definition. The etch control instructions define control parameters for various aspects of the system 600 that are employed by the process control component 642 in connection with performing the desired etch described in the etch definition. In an exemplary embodiment, the etch control instructions include a plurality of positions of the focal spot 644 of the laser 604. In other examples, the etch control instructions can include data indicative of a composition of the etching solution 610, a temperature of the etching solution 610, a voltage output of the voltage source 620, etc.

In the exemplary system 600, the beam 609 is emitted into the backside surface 628 of the semiconductor 608 to avoid scattering of the beam 609 by already-etched features in the semiconductor 608, such as the feature 646. Scattering of the beam 609 by etched features in the semiconductor 608 can usually by avoided by illumination the semiconductor 608 with the laser 604 from the backside 628 and etching features nearest the etching surface 612 first before etching features that are further away from the etching surface 612. However, for more complicated three-dimensional structures, it may be necessary to etch features in a different order to avoid scattering of the beam 609. The etch modeling component 658 can be configured to generate the etch control instructions in order to minimize occasions of the beam 609 crossing an already-etched feature in the semiconductor 608.

In exemplary embodiments, the etch modeling component 658 generates the etch control instructions based upon a physics model 660 that is configured to output predictions of migration of holes within the semiconductor 608. In an example, a desired etch location is provided to the physics model 660 (e.g., as indicated in an etch definition provided to the etch modeling component 658) and the physics model 660 outputs a prediction that comprises an illumination location, wherein the prediction indicates that a hole generated at the illumination location is expected to migrate to the desired etch location. Stated differently, the physics model 660 receives a location of desired etching of the semiconductor 608 and outputs a prediction of where the focal spot 644 of the laser 604 can be positioned to result in the desired etch.

The physics model 660 generates an illumination location prediction for a desired etch location based upon various parameters that affect motion of holes in the semiconductor 608. Such physical effects include, but are not limited to, charge-carrier diffusion, an induced electric field within the semiconductor 608 (e.g., as caused by a voltage established between the electrodes 622, 624), a current flow I through an electrochemical cell that comprises the conductive material 626, the semiconductor 608, the etching solution 610, the electrodes 622, 624, and the voltage source 620, etc. In connection with generating an illumination location prediction, the physics model 660 can further model effects due to these parameters based on other underlying data that may affect a modeled physical process. For example, the physics model 660 can model effects of charge-carrier diffusion based on a composition of the semiconductor 608 and concentrations of dopants or other impurities in the semiconductor 608. In another example, the physics model 660 can model effects of an induced electric field based upon a voltage applied between the electrodes 622, 624.

The physics model 660, in addition to receiving data pertaining to desired etch parameters (e.g., as specified in an etch definition submitted to the etch modeling component 658), receives data pertaining to a present state of one or more operating parameters of the system 600. For example, the process control component 642 can in real-time output data to the physics model 660, the data indicative of the current flow I, the current flow I indicative of a reaction rate of the etching reaction (e.g., the reaction described by Equations 1 and 2 above). Hence, the physics model 660 can continually generate updated predictions of illumination locations for desirably etched features based on data pertaining to a current state of the system 600. The etch modeling component 658 can generate updated control instructions based upon the predictions and transmit the updated control instructions to the process control component 642 to facilitate control of the system 600 by the process control component 642 based on up-to-date information about system state.

In other exemplary embodiments, the physics model 660 can be configured to generate an illumination location prediction based upon simulation results 662 that are stored in the data store 640. In an embodiment, the simulation results 662 include results of a large number (e.g., hundreds or thousands or more) of simulated etches of a semiconductor according to various etch parameters. The physics model 660 can be configured to execute machine learning algorithms over the simulation results 662 to identify results of a simulated etch that exhibit a similar etch pattern to a desired etch indicated in an etch definition received by the etch modeling component 658. The physics model 660 can then output an illumination location prediction based on the identified results.

While certain examples of physical effects that are modeled by the physics model 660 are described herein, it is contemplated that the physics model 660 can model substantially any physical process that can affect a resultant etch location of holes generated by the focal spot 644 of the laser 604 at an illumination location.

It is to be understood that the systems and methods for selective electrochemical etching of various semiconductors are suitable for etching features of various sizes. For example, features can be etched in accordance with the technologies described herein to have a size on the order of 10 nanometers to 1 micron, on the order of 10 microns to 1 millimeter, or features of arbitrarily large size.

Figure 13:
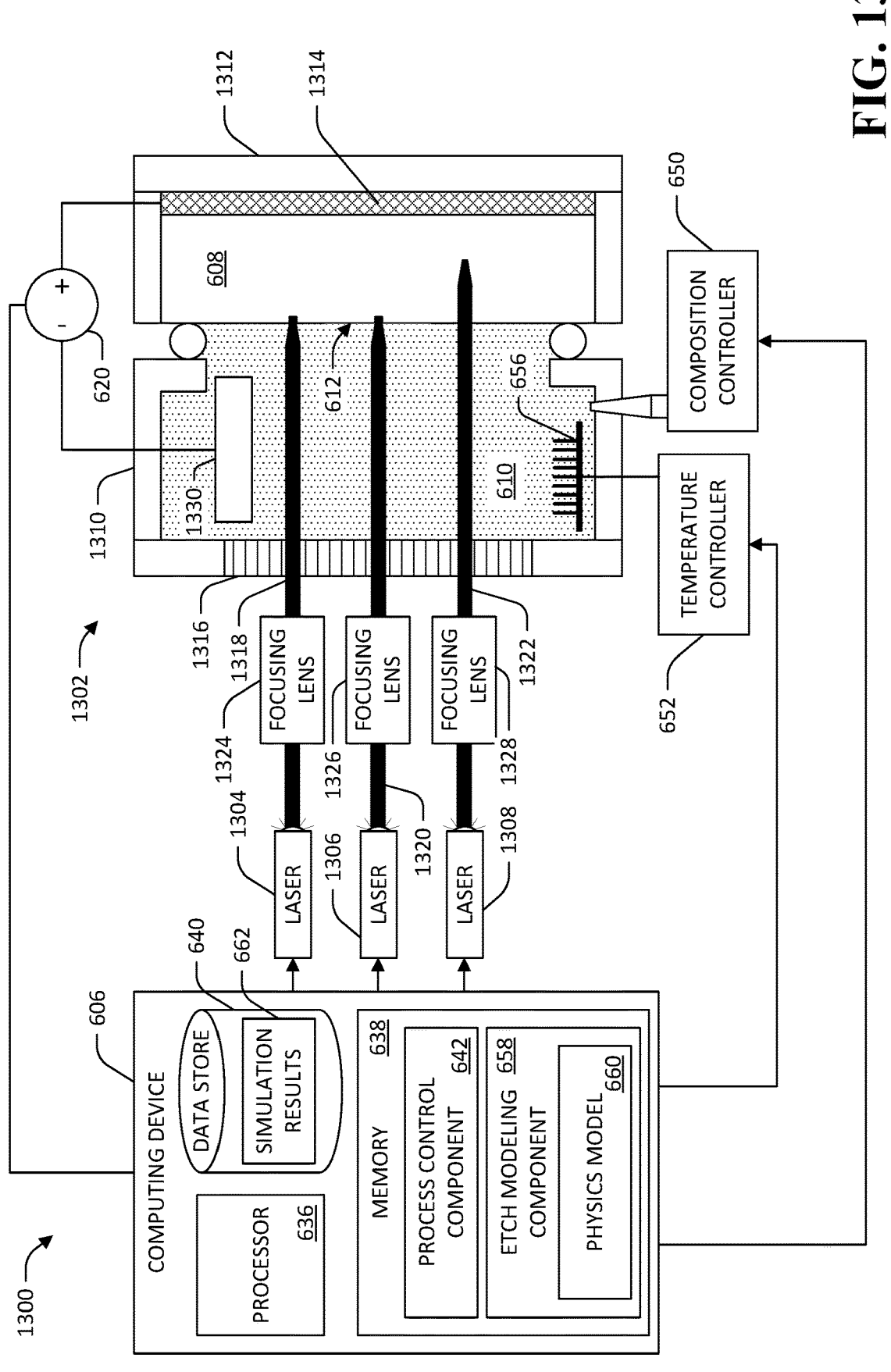
FIG. 13 is a diagram of another exemplary system that facilitates selective etching of a semiconductor controlled by a plurality of sub-bandgap-energy lasers.

While various aspects pertaining to an exemplary system 600 operable in connection with selective etching of a semiconductor are described in detail above, it is to be understood that other configurations are possible and contemplated as being within the scope of the present disclosure. Referring now to FIG. 13, another exemplary system 1300 is shown wherein the semiconductor 608 is contained in an etching chamber 1302 that is configured for frontside illumination by a plurality of sub-bandgap-energy lasers 1304-1308. The etching chamber 1302 includes a first containment vessel 1310 that contains the etching solution 610 and a second containment vessel 1312 that contains the semiconductor 608 and a conductive element 1314. The first containment vessel 1310 further comprises a window 1316 through which beams 1318-1322 emitted by respective lasers 1304-1308 are focused by respective focusing lenses 1324-1328 toward the frontside etching surface 612 of the semiconductor 608. It is to be understood that while the beams 1318-1322 are emitted toward the frontside surface 612 of the semiconductor 608, the beams 1318-1322 may be focused to respective focal spots within a body of the semiconductor 608 and underneath the surface 612. In the exemplary system 1300, the voltage source 620 is connected between the conductive element 1314 that makes electrical contact with the backside 628 of the semiconductor 608 and an electrode 1330 that is positioned in the first containment vessel 1310.

The process control component 642 of the computing device 606 can be configured to independently control the plurality of lasers 1304-1308 in order to facilitate faster etching of the semiconductor 608. For instance, since etching of the semiconductor 608 by the etching solution 610 is driven by holes that facilitate the etching reaction, simultaneous generation of holes at multiple locations in the semiconductor 608 by the lasers 1304-1308 enables several features to be etched simultaneously. It is to be understood that substantially any number of lasers may be included in a system for selective electrochemical etching of a semiconductor and controlled by the process control component 642. In other example it may be desirable for the process control component 642 to control a plurality of lasers to operate in parallel such that a same feature may be simultaneously etched a plurality of times in the semiconductor 608.

Figure 14:
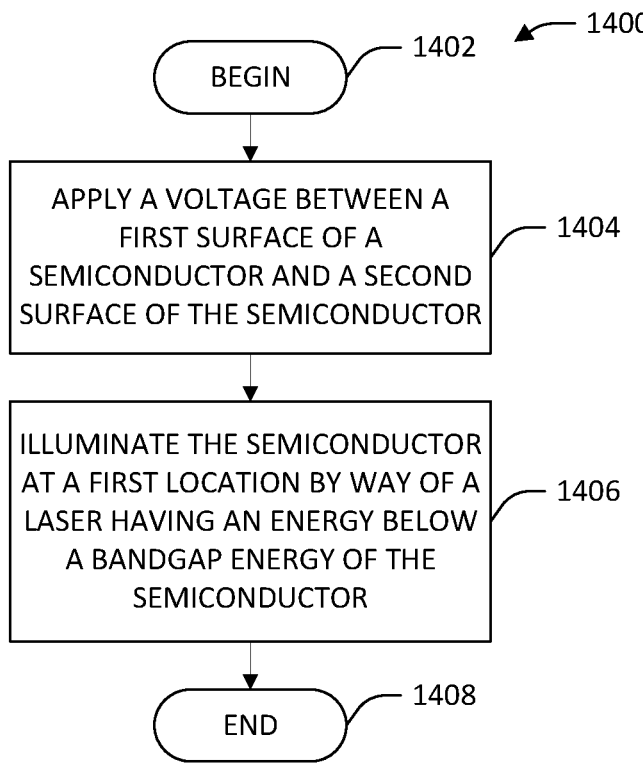
FIG. 14 is a flow diagram that illustrates an exemplary methodology for selective semiconductor etching controlled by a sub-bandgap-energy laser.

FIG. 14 illustrates an exemplary methodology relating to selective semiconductor etching driven by sub-bandgap-energy illumination of the semiconductor. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, some of the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodology can be stored in a computer-readable medium, displayed on a display device, and/or the like.

Referring now to FIG. 14, a methodology 1400 that facilitates selective etching of a semiconductor by sub-bandgap-energy illumination of the semiconductor is illustrated. The methodology 1400 begins at 1402, and at 1404 a voltage is applied between a first surface of a semiconductor and a second surface of the semiconductor. By way of example, the voltage can be applied between the first surface and the second surface by applying a voltage between electrodes that are immersed in conductive solutions that respectively make contact with the first and second surfaces of the semiconductor (e.g., the electrodes 622, 624 shown in the exemplary system 600). At 1406, the semiconductor is illuminated at a first location by way of a laser that emits light that has an energy below a bandgap energy of the semiconductor. The laser is focused to a focal spot sufficiently intense to cause a hole to be generated at the first location in the semiconductor, wherein etching of the semiconductor occurs at a second location based upon the hole being generated at the first location. The methodology then ends at 1408.

Figure 15:
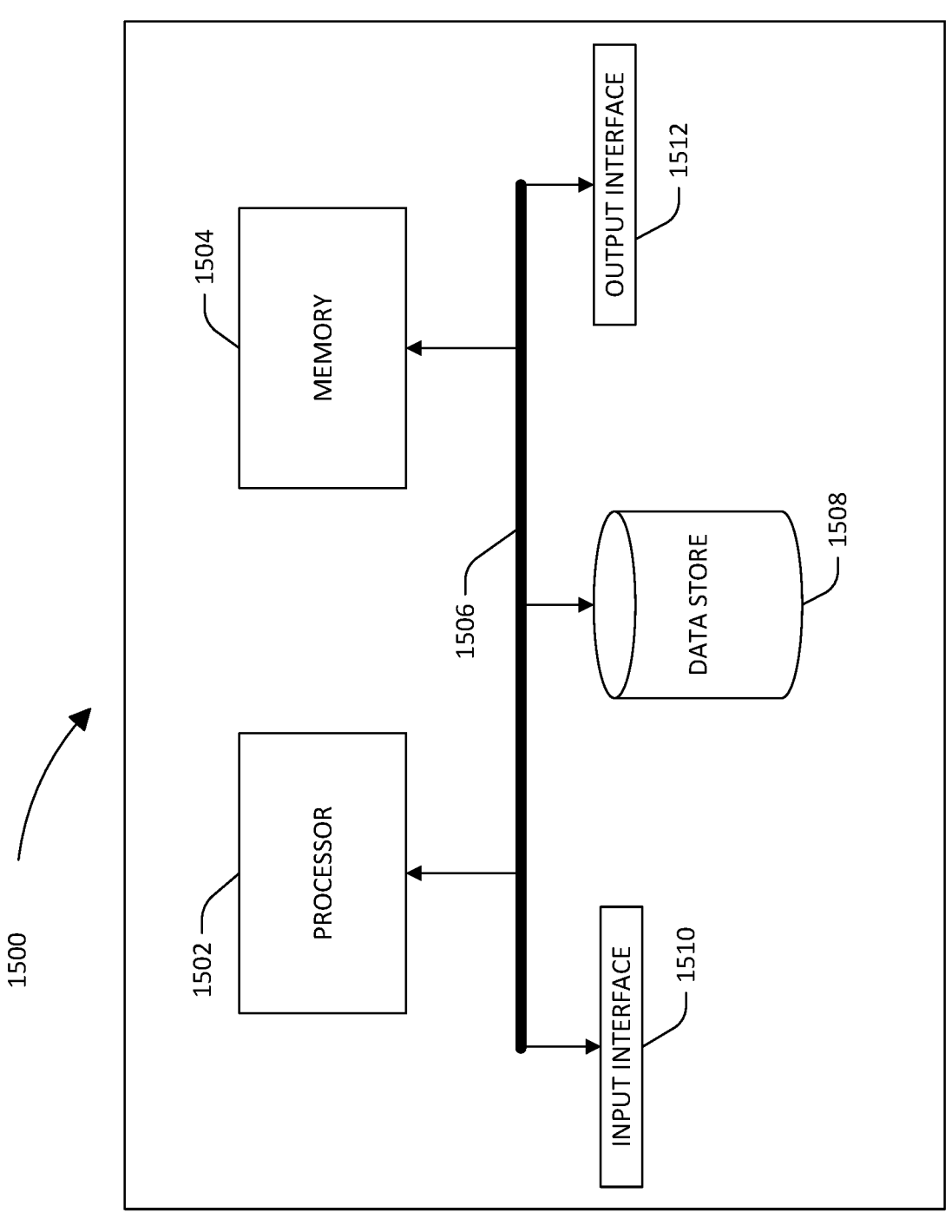
FIG. 15 is an exemplary computing system.

Referring now to FIG. 15, a high-level illustration of an exemplary computing device 1500 that can be used in accordance with the systems and methodologies disclosed herein is illustrated. For instance, the computing device 1500 may be used in a system that controls operation of a system for selective semiconductor etching (e.g., the system 600, the system 1300). By way of another example, the computing device 1500 can be used in a system that performs simulations of charge-carrier migration within a semiconductor based upon a physics model. The computing device 1500 includes at least one processor 1502 that executes instructions that are stored in a memory 1504. The instructions may be, for instance, instructions for implementing functionality described as being carried out by one or more components discussed above or instructions for implementing one or more of the methods described above. The processor 1502 may access the memory 1504 by way of a system bus 1506. In addition to storing executable instructions, the memory 1504 may also store simulation results, etching definitions, states of various process parameters of a selective etching system, etc.

The computing device 1500 additionally includes a data store 1508 that is accessible by the processor 1502 by way of the system bus 1506. The data store 1508 may include executable instructions, simulation results, etc. The computing device 1500 also includes an input interface 1510 that allows external devices to communicate with the computing device 1500. For instance, the input interface 1510 may be used to receive instructions from an external computer device, from a user, etc. The computing device 1500 also includes an output interface 1512 that interfaces the computing device 1500 with one or more external devices. For example, the computing device 1500 may display text, images, etc. by way of the output interface 1512.

It is contemplated that the external devices that communicate with the computing device 1500 via the input interface 1510 and the output interface 1512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1500 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1500 may be a distributed system. Thus, for instance, several devices may be in communication by way of a network connection and may collectively perform tasks described as being performed by the computing device 1500.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for manufacturing a scaffold for supporting tissue growth, the method comprising:
controlling electrochemical etching of a semiconductor by way of a laser to manufacture the scaffold, wherein the laser emits a beam of light having an energy below a bandgap energy of the semiconductor, wherein controlling the electrochemical etching of the semiconductor comprises focusing the beam in the semiconductor to cause multi-photon absorption (MPA) within the semiconductor, wherein controlling the electrochemical etching of the semiconductor further comprises variably controlling a voltage source to establish an electric field within the semiconductor, wherein a focal spot of the beam and the electric field within the semiconductor are controlled based on a predicted migration of charge carriers within the semiconductor to form a feature having a desired characteristic etched in the semiconductor, wherein the scaffold comprises:
a first capillary element;
a second capillary element; and
a connective element that spans a distance between the first capillary element and the second capillary element.

2. The method of claim 1, wherein the semiconductor comprises silicon.

3. The method of claim 1, further comprising generating a computer-aided design (CAD) model based upon a scan of at least a portion of a body of a patient, the CAD model representative of at least one of an organ or a capillary structure in the body of the patient, wherein the controlling the electrochemical etching of the semiconductor is based upon the CAD model.

4. The method of claim 1, wherein the first capillary element has a diameter of less than 25 microns.

5. The method of claim 1, wherein the first capillary element comprises a wall having a thickness of less than 2 microns.

6. The method of claim 1, wherein the first capillary element and the second capillary element are separated by a distance of less than 100 microns.

7. The method of claim 1, wherein the first capillary comprises a wall, the wall having a plurality of holes formed therein.

8. The method of claim 7, the plurality of holes including a first hole, the first hole having a width between 10 nanometers and 100 nanometers.

9. The method of claim 7, the plurality of holes including a first hole, the first hole having a width between 5 microns and 80 microns.

10. The method of claim 1, the electrochemical etching of the semiconductor controlled such that the scaffold further comprises:
an arteriole element; and
a venule element, wherein the first capillary element and the second capillary element are each connected between the arteriole element and the venule element.

11. The method of claim 1, the electrochemical etching of the semiconductor controlled such that the scaffold further comprises a plurality of connective elements, the plurality of connective elements including the connective element, wherein each of the plurality of connective elements connects the first capillary to the second capillary.

12. The method of claim 1, wherein variably controlling the voltage source comprises applying a bias voltage of less than 2 volts to the semiconductor during the electrochemical etching of the semiconductor.

13. A method for growing tissues comprising:
controlling electrochemical etching of a semiconductor by way of a laser to manufacture a scaffold, wherein the laser emits a beam of light having an energy below a bandgap energy of the semiconductor, wherein controlling the electrochemical etching of the semiconductor comprises focusing the beam in the semiconductor to cause multi-photon absorption (MPA) within the semiconductor, wherein controlling the electrochemical etching of the semiconductor further comprises variably controlling a voltage source to establish an electric field within the semiconductor, wherein a focal spot of the beam and the electric field within the semiconductor are controlled based on a predicted migration of charge carriers within the semiconductor to to form a feature having a desired characteristic etched in the semiconductor, wherein the scaffold comprises:
a first capillary element;
a second capillary element; and
a connective element that spans a distance between the first capillary element and the second capillary element; and
introducing a cellular sample into the first capillary element.

14. The method of claim 13, further comprising pumping a fluid through an interior of the first capillary element, the fluid comprises a nutrient.

15. The method of claim 13, wherein the cellular sample comprises endothelial cells.

16. The method of claim 13, wherein the cellular sample comprises stem cells.

17. The method of claim 1, wherein the characteristic of the feature comprises at least one of a size of the feature, a shape of the feature, or a location of the feature.

* * * * *